US012728002B2

(12) United States Patent
Dvorsky et al.

(10) Patent No.: US 12,728,002 B2
(45) Date of Patent: Sep. 8, 2026

(54) SYSTEMS AND METHODS FOR ESTIMATING OUTER DIAMETERS OF PROSTHETIC VALVES

(71) Applicant: EDWARDS LIFESCIENCES CORPORATION, Irvine, CA (US)

(72) Inventors: Anatoly Dvorsky, Haifa (IL); Yara Khader, Nazareth-Illit (IL)

(73) Assignee: Edwards Lifesciences Corporation, Irvine, CA (US)

( * ) Notice: Subject to any disclaimer, the term of this patent is extended or adjusted under 35 U.S.C. 154(b) by 312 days.

(21) Appl. No.: 18/139,183

(22) Filed: Apr. 25, 2023

(65) Prior Publication Data

US 2023/0277319 A1 Sep. 7, 2023

Related U.S. Application Data

(63) Continuation of application No. PCT/US2021/056756, filed on Oct. 27, 2021.

(Continued)

(51) Int. Cl.

*A61F 2/24* (2006.01)
*G06T 7/00* (2017.01)
*G06T 7/62* (2017.01)

(52) U.S. Cl.

CPC .......... *A61F 2/2472* (2013.01); *G06T 7/0012* (2013.01); *G06T 7/62* (2017.01); *G06T 2207/30052* (2013.01)

(58) Field of Classification Search

CPC .... A61F 2/2472; A61F 2/2418; A61F 2/2412; A61F 2/2409; A61F 2/2436;

(Continued)

(56) References Cited

U.S. PATENT DOCUMENTS

| | | |
|---|---|---|
| 3,409,013 A | 11/1968 | Berry |
| 3,548,417 A | 12/1970 | Kisher |

(Continued)

FOREIGN PATENT DOCUMENTS

| | | |
|---|---|---|
| DE | 0144167 C | 9/1903 |
| DE | 2246526 A1 | 3/1973 |

(Continued)

OTHER PUBLICATIONS

HR. Andersen, et al. "Transluminal Implantation of Artificial Heart Valve. Description of a New Expandable Aortic Valve and Initial Results with implantation by Catheter Technique in Closed Chest Pig,"European Heart Journal, No. 13. pp. 704-708. 1992.

(Continued)

*Primary Examiner* — Matthew C Bella
*Assistant Examiner* — Daniel J. Santos
(74) *Attorney, Agent, or Firm* — Klarquist Sparkman LLP

(57) ABSTRACT

The present invention relates to systems and methods for estimating prosthetic valve expansion diameter, and in particular, for system and methods for analyzing images acquired during prosthetic valve expansion, to identify structural components of the valve, determine dimensions thereof, and estimate at least one outer diameter of the prosthetic valve, and potentially a plurality of outer diameter along different axial positions of the prosthetic valve.

22 Claims, 13 Drawing Sheets

Related U.S. Application Data

(60) Provisional application No. 63/106,817, filed on Oct. 28, 2020.

(58) Field of Classification Search
CPC ..................... G06T 7/0012; G06T 7/62; G06T 2207/30052; G06T 2207/10121; G06T 2207/30048
USPC .......................................................... 382/100
See application file for complete search history.

(56) References Cited

U.S. PATENT DOCUMENTS 3,587,115 A 6/1971 Shiley
3,657,744 A 4/1972 Ersek
3,671,979 A 6/1972 Moulopoulos
3,714,671 A 2/1973 Edwards et al.
3,755,823 A 9/1973 Hancock
4,035,849 A 7/1977 Angell et al.
4,056,854 A 11/1977 Boretos et al.
4,106,129 A 8/1978 Carpentier et al.
4,222,126 A 9/1980 Boretos et al.
4,265,694 A 5/1981 Boretos et al.
4,297,749 A 11/1981 Davis et al.
4,339,831 A 7/1982 Johnson
4,343,048 A 8/1982 Ross et al.
4,345,340 A 8/1982 Rosen
4,373,216 A 2/1983 Klawitter
4,406,022 A 9/1983 Roy
4,441,216 A 4/1984 Ionescu et al.
4,470,157 A 9/1984 Love
4,535,483 A 8/1985 Klawitter et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,820,299 A 4/1989 Philippe et al.
4,829,990 A 5/1989 Thuroff et al.
4,851,001 A 7/1989 Taheri
4,856,516 A 8/1989 Hillstead
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,152,771 A 10/1992 Sabbaghian et al.
5,163,953 A 11/1992 Vince
5,167,628 A 12/1992 Boyles
5,192,297 A 3/1993 Hull
5,266,073 A 11/1993 Wall
5,282,847 A 2/1994 Trescony et al.
5,295,958 A 3/1994 Shturman
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,552 A 5/1995 Andersen et al.
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,558,644 A 9/1996 Boyd et al.
5,571,175 A 11/1996 Vanney et al.
5,584,803 A 12/1996 Stevens et al.
5,591,185 A 1/1997 Kilmer et al.
5,591,195 A 1/1997 Taheri et al.
5,607,464 A 3/1997 Trescony et al.
5,609,626 A 3/1997 Quijano et al.
5,628,792 A 5/1997 Lentell
5,639,274 A 6/1997 Fischell et al.
5,665,115 A 9/1997 Cragg
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,925,063 A 7/1999 Khosravi
5,957,949 A 9/1999 Leonhardt et al.
6,027,525 A 2/2000 Suh et al.
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,102 B1 6/2001 Jayaraman
6,299,637 B1 10/2001 Shaolian et al.
6,302,906 B1 10/2001 Goecoechea et al.
6,350,277 B1 2/2002 Kocur
6,352,547 B1 3/2002 Brown et al.
6,425,916 B1 7/2002 Garrison et al.
6,440,764 B1 8/2002 Focht et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.
6,527,979 B2 3/2003 Constantz
6,569,196 B1 5/2003 Vesely
6,582,462 B1 6/2003 Andersen et al.
6,605,112 B1 8/2003 Moll et al.
6,652,578 B2 11/2003 Bailey et al.
6,689,123 B2 2/2004 Pinchasik
6,716,244 B2 4/2004 Klaco
6,730,118 B2 5/2004 Spenser et al.
6,733,525 B2 5/2004 Yang et al.
6,767,362 B2 7/2004 Schreck
6,769,161 B2 8/2004 Brown et al.
6,783,542 B2 8/2004 Eidenschink
6,830,584 B1 12/2004 Seguin
6,878,162 B2 4/2005 Bales et al.
6,893,460 B2 5/2005 Spenser et al.
6,908,481 B2 6/2005 Cribier
6,936,067 B2 8/2005 Buchanan
7,018,406 B2 3/2006 Seguin et al.
7,018,408 B2 3/2006 Bailey et al.
7,096,554 B2 8/2006 Austin et al.
7,225,518 B2 6/2007 Eidenschink et al.
7,276,078 B2 10/2007 Spenser et al.
7,276,084 B2 10/2007 Yang et al.

(56) References Cited

U.S. PATENT DOCUMENTS 7,318,278 B2 1/2008 Zhang et al.
7,374,571 B2 5/2008 Pease et al.
7,393,360 B2 7/2008 Spenser et al.
7,462,191 B2 12/2008 Spenser et al.
7,510,575 B2 3/2009 Spenser et al.
7,563,280 B2 7/2009 Anderson et al.
7,585,321 B2 9/2009 Cribier
7,618,446 B2 11/2009 Andersen et al.
7,618,447 B2 11/2009 Case et al.
7,655,034 B2 2/2010 Mitchell et al.
7,785,366 B2 8/2010 Maurer et al.
7,959,672 B2 6/2011 Salahieh et al.
7,993,394 B2 8/2011 Hariton et al.
8,029,556 B2 10/2011 Rowe
8,167,932 B2 5/2012 Bourang et al.
8,291,570 B2 10/2012 Eidenschink et al.
8,449,606 B2 5/2013 Eliasen et al.
8,454,685 B2 6/2013 Hariton et al.
8,652,203 B2 2/2014 Quadri et al.
8,747,463 B2 6/2014 Fogarty et al.
9,078,781 B2 7/2015 Ryan et al.
11,224,509 B2 1/2022 Dasi et al.
2001/0021872 A1 9/2001 Bailey et al.
2002/0026094 A1 2/2002 Roth
2002/0032481 A1 3/2002 Gabbay
2002/0138135 A1 9/2002 Duerig et al.
2002/0173842 A1 11/2002 Buchanan
2003/0050694 A1 3/2003 Yang et al.
2003/0100939 A1 5/2003 Yodfat et al.
2003/0158597 A1 8/2003 Quiachon et al.
2003/0212454 A1 11/2003 Scott et al.
2004/0039436 A1 2/2004 Spenser et al.
2004/0167619 A1* 8/2004 Case et al. ................ A61F 2/06 623/1.34
2004/0186563 A1 9/2004 Lobbi
2004/0186565 A1 9/2004 Schreck
2004/0260389 A1 12/2004 Case et al.
2005/0010285 A1 1/2005 Lambrecht et al.
2005/0075725 A1 4/2005 Rowe
2005/0075728 A1 4/2005 Nguyen et al.
2005/0096736 A1 5/2005 Osse et al.
2005/0188525 A1 9/2005 Weber et al.
2005/0203614 A1 9/2005 Forster et al.
2005/0203617 A1 9/2005 Forster et al.
2005/0234546 A1 10/2005 Nugent et al.
2006/0004469 A1 1/2006 Sokel
2006/0025857 A1 2/2006 Bergheim et al.
2006/0058872 A1 3/2006 Salahieh et al.
2006/0074484 A1 4/2006 Huber
2006/0149350 A1 7/2006 Patel et al.
2006/0183383 A1 8/2006 Asmus et al.
2006/0229719 A1 10/2006 Marquez et al.
2006/0259137 A1 11/2006 Artof et al.
2006/0287717 A1 12/2006 Rowe et al.
2007/0005131 A1 1/2007 Taylor
2007/0010876 A1 1/2007 Salahieh et al.
2007/0010877 A1 1/2007 Salahieh et al.
2007/0112422 A1 5/2007 Dehdashtian
2007/0162102 A1 7/2007 Ryan et al.
2007/0203503 A1 8/2007 Salahieh et al.
2007/0203575 A1 8/2007 Forster et al.
2007/0203576 A1 8/2007 Lee et al.
2007/0213813 A1 9/2007 Von Segesser et al.
2007/0233228 A1 10/2007 Eberhardt et al.
2007/0260305 A1 11/2007 Drews et al.
2007/0265700 A1 11/2007 Eliasen et al.
2008/0114442 A1 5/2008 Mitchell et al.
2008/0125853 A1 5/2008 Bailey et al.
2008/0154355 A1 6/2008 Benichou et al.
2008/0183271 A1 7/2008 Frawley et al.
2008/0243245 A1 10/2008 Thambar et al.
2008/0275537 A1 11/2008 Limon
2009/0125118 A1 5/2009 Gong
2009/0157175 A1 6/2009 Benichou
2009/0276040 A1 11/2009 Rowe et al.
2009/0281619 A1 11/2009 Le et al.
2009/0299452 A1 12/2009 Eidenschink et al.
2009/0319037 A1 12/2009 Rowe et al.
2010/0049313 A1 2/2010 Alon et al.
2010/0168844 A1 7/2010 Toomes et al.
2010/0198347 A1 8/2010 Zakay et al.
2010/0204781 A1 8/2010 Alkhatib
2010/0222671 A1* 9/2010 Cohen et al. ............ A61B 5/05 600/424
2011/0015729 A1 1/2011 Jimenez et al.
2011/0066224 A1 3/2011 White
2011/0137397 A1 6/2011 Chau et al.
2011/0218619 A1 9/2011 Benichou et al.
2011/0319991 A1 12/2011 Hariton et al.
2012/0089223 A1 4/2012 Nguyen et al.
2012/0101571 A1 4/2012 Thambar et al.
2012/0123529 A1 5/2012 Levi et al.
2012/0259409 A1 10/2012 Nguyen et al.
2013/0023985 A1 1/2013 Khairkhahan et al.
2013/0046373 A1 2/2013 Cartledge et al.
2013/0150956 A1 6/2013 Yohanan et al.
2013/0166017 A1 6/2013 Cartledge et al.
2013/0190857 A1 7/2013 Mitra et al.
2013/0274873 A1 10/2013 Delaloye et al.
2013/0310926 A1 11/2013 Hariton
2013/0317598 A1 11/2013 Rowe et al.
2013/0331929 A1 12/2013 Mitra et al.
2014/0194981 A1 7/2014 Menk et al.
2014/0200661 A1 7/2014 Pintor et al.
2014/0209238 A1 7/2014 Bonyuet et al.
2014/0222136 A1 8/2014 Geist et al.
2014/0277417 A1 9/2014 Schraut et al.
2014/0277419 A1 9/2014 Garde et al.
2014/0277424 A1 9/2014 Oslund
2014/0277563 A1 9/2014 White
2014/0330372 A1 11/2014 Weston et al.
2014/0343671 A1 11/2014 Yohanan et al.
2014/0350667 A1 11/2014 Braido et al.
2015/0073545 A1 3/2015 Braido
2015/0073546 A1 3/2015 Braido
2017/0116751 A1* 4/2017 Speidel et al. ........ G06T 7/2046
2018/0110618 A1* 4/2018 Cartledge et al. .... A61F 2/2418

FOREIGN PATENT DOCUMENTS

DE 19532846 A1 3/1997
DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
EP 0103546 A1 3/1984
EP 0850607 A1 7/1998
EP 1057460 A1 12/2000
EP 1088529 A2 4/2001
EP 1570809 A1 9/2005
FR 2788217 A1 7/2000
FR 2815844 A1 5/2002
GB 2056023 A 3/1981
SU 1271508 A1 11/1986
WO 9117720 A1 11/1991
WO 9217118 A1 10/1992
WO 9301768 A1 2/1993
WO 9724080 A1 7/1997
WO 9829057 A1 7/1998
WO 9930646 A1 6/1999
WO 9933414 A1 7/1999
WO 9940964 A1 8/1999
WO 9947075 A1 9/1999
WO 0018333 A1 4/2000
WO 0041652 A1 7/2000
WO 0047139 A1 8/2000
WO 0135878 A2 5/2001
WO 0149213 A2 7/2001
WO 0154624 A1 8/2001
WO 0154625 A1 8/2001
WO 0162189 A1 8/2001

(56) References Cited

FOREIGN PATENT DOCUMENTS

| | | | |
|---|---|---|---|
| WO | 0164137 | A1 | 9/2001 |
| WO | 0176510 | A2 | 10/2001 |
| WO | 0222054 | A1 | 3/2002 |
| WO | 0236048 | A1 | 5/2002 |
| WO | 0241789 | A2 | 5/2002 |
| WO | 0243620 | A1 | 6/2002 |
| WO | 0247575 | A2 | 6/2002 |
| WO | 0249540 | A2 | 6/2002 |
| WO | 03047468 | A1 | 6/2003 |
| WO | 2005034812 | A1 | 4/2005 |
| WO | 2005055883 | A1 | 6/2005 |
| WO | 2005084595 | A1 | 9/2005 |
| WO | 2005102015 | A2 | 11/2005 |
| WO | 2006014233 | A2 | 2/2006 |
| WO | 2006032051 | A2 | 3/2006 |
| WO | 2006034008 | A2 | 3/2006 |
| WO | 2006111391 | A1 | 10/2006 |
| WO | 2006127089 | A1 | 11/2006 |
| WO | 2006138173 | A2 | 12/2006 |
| WO | 2007047488 | A2 | 4/2007 |
| WO | 2007067942 | A1 | 6/2007 |
| WO | 2007097983 | A2 | 8/2007 |
| WO | 2008005405 | A2 | 1/2008 |
| WO | 2008015257 | A2 | 2/2008 |
| WO | 2008035337 | A2 | 3/2008 |
| WO | 2008091515 | A2 | 7/2008 |
| WO | 2008147964 | A1 | 12/2008 |
| WO | 2008150529 | A1 | 12/2008 |
| WO | 2009033469 | A1 | 3/2009 |
| WO | 2009042196 | A2 | 4/2009 |
| WO | 2009053497 | A1 | 4/2009 |
| WO | 2009061389 | A2 | 5/2009 |
| WO | 2009094188 | A2 | 7/2009 |
| WO | 2009116041 | A2 | 9/2009 |
| WO | 2009149462 | A2 | 12/2009 |
| WO | 2010011699 | A2 | 1/2010 |
| WO | 2010121076 | A2 | 10/2010 |
| WO | 2013106585 | A1 | 7/2013 |
| WO | 2015085218 | A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5): 1120-6. Epub Apr. 7, 2011.

Wagner M., et al., "A Real-time System for Prosthetic Valve Tracking," Progress in Biomedical Optics and Imaging, SPIE—International Society for Optical Engineering, Bellingham, WA, US, Mar. 13, 2018, vol. 10576, pp. 105761A-105761A, DOI: 10.1117/12.2293837 ISSN: 1605-7422, ISBN: 978-1-5106-0027-0, XP060106740.

* cited by examiner

SYSTEMS AND METHODS FOR ESTIMATING OUTER DIAMETERS OF PROSTHETIC VALVES

CROSS REFERENCE TO RELATED APPLICATIONS

This application is a continuation of International Application No. PCT/US2021/056756, filed Oct. 27, 2021, which claims benefit of U.S. Provisional Application No. 63/106,817, filed on Oct. 28, 2020, the contents of each of which are herein incorporated by reference in their entirety.

FIELD OF THE INVENTION

The present invention relates to systems and methods for estimating prosthetic valve expansion diameter, and in particular, for system and methods for analyzing images acquired during prosthetic valve expansion, to identify structural components of the valve, determine dimensions thereof, and estimate at least one outer diameter of the prosthetic valve, and potentially a plurality of outer diameter along different axial positions of the prosthetic valve.

BACKGROUND OF THE INVENTION

Native heart valves, such as the aortic, pulmonary and mitral valves, function to assure adequate directional flow from and to the heart, and between the heart's chambers, to supply blood to the whole cardiovascular system. Various valvular diseases can render the valves ineffective and require replacement with artificial valves. Surgical procedures can be performed to repair or replace a heart valve. Surgeries are prone to an abundance of clinical complications, hence alternative less invasive techniques of delivering a prosthetic heart valve over a catheter and implanting it over the native malfunctioning valve, have been developed over the years.

Mechanically expandable valves are a category of prosthetic valves that rely on a mechanical actuation mechanism for expansion. The actuation mechanism usually includes a plurality of actuation/locking assemblies, releasably connected to respective actuation members of the valve delivery system, controlled via the handle for actuating the assemblies to expand the valve to a desired diameter. The assemblies may optionally lock the valve's position to prevent undesired recompression thereof, and disconnection of the delivery system's actuation member from the valve actuation/locking assemblies, to enable retrieval thereof once the valve is properly positioned at the desired site of implantation.

When implanting a prosthetic valve, such as a mechanically expandable valve, it is desirable to expand the valve to a maximum size allowed by the patient's anatomical considerations, in order to avoid paravalvular leakage or other unfavorable hemodynamic phenomena across the valve that may be associated with a mismatch between the valve's expansion diameter and the surrounding tissue, while mitigating the risk of annular rupture that may result from over-expansion. To ensure optimal implantation size, the diameter of the prosthetic valve should be monitored in real-time during the implantation procedure.

SUMMARY OF THE INVENTION

The present disclosure is directed toward devices, assemblies and methods for estimating at least one outer diameter of a prosthetic valve during prosthetic valve implantation and expansion procedures. Estimation of prosthetic valve diameters, that may be provided in real-time during expansion thereof, can ensure proper implantation of the prosthetic valve within a designated site of implantation, such as the site of malfunctioning native valve.

According to one aspect of the inventions, there is provided a method of estimating at least one outer diameter of a prosthetic valve, comprising a step of acquiring, by an imaging device, an image of the prosthetic valve. The method further comprises a step of analyzing, by a control circuitry, the image to determine at least one lateral width. The method further comprises a step of retrieving, by the control circuitry, a length of the constant-length structural component and associate the length with the identified constant-length structural component.

The method further comprises a step of estimating at least one outer diameter of the prosthetic valve, based at least in part on the at least one lateral width determined at the axial position of the estimated outer diameter, and the length of the constant-length structural component.

According to some examples, the step of analyzing the image to determine at least one lateral width further comprises identifying structural components of the prosthetic valve, prior to determining at least one lateral width.

According to some examples, the step of identifying structural components comprises identifying strut segments of the prosthetic valve.

According to some examples, the step of identifying structural components comprises identifying junctions of the prosthetic valve.

According to some examples, the step of identifying structural components comprises identification of at least one cell, wherein the at least one lateral width extends between two laterally aligned junctions of the same cell.

According to some examples, the at least one identified cell comprises at least two cell columns, wherein the plurality of lateral widths comprises at least one lateral width extending between lateral junctions of each of the two cell columns.

According to some examples, the step of analyzing the image to determine at least one lateral width further comprises determining at least one opening angle defined between two intersecting strut segments, the opening angle facing the lateral width, wherein the lateral width is calculated from the opening angle and a length of a strut segment.

According to some examples, the step of analyzing the image to determine at least one lateral width further comprises determining at least one opening angle defined between a strut segment and the lateral width, wherein the lateral width is calculated from the opening angle and a length of a strut segment.

According to some examples, the prosthetic valve comprises a plurality of threaded rods and plurality of nuts, each nut screwed on to a respective threaded rod, wherein the step of identifying structural components comprises identifying the plurality of nuts of the prosthetic valve, and wherein the at least one lateral width extends between a respective pair of the identified nuts of the prosthetic valve.

According to some examples, the at least one lateral width comprises a plurality of lateral widths, each positioned at a different axial position along the length of the prosthetic valve.

According to some examples, the method further comprises a step of analyzing, by a control circuitry, the image to determine at least one vertical height, wherein the at least one vertical height comprises a plurality of vertical heights, wherein the method further comprises a step of comparing between the vertical heights and generating data indicative of whether the expansion of the prosthetic valve is non-even.

According to some examples, the constant-length structural component is an outer member of an expansion and locking assembly coupled to a frame of the prosthetic valve.

According to some examples, the constant-length structural component is a strut segment of the prosthetic valve.

According to some examples, the step of estimating at least one outer diameter comprises calculating a diameter of a circumcircle surrounding an internal polygon defined between junctions disposed around the prosthetic valve at a corresponding lateral plane, wherein the length of each of the edges of the internal polygon is the lateral width determined at the axial position of the lateral plane, and wherein the calculation further includes conversion of distances from pixels to length units based at least in part on the length of the constant-length structural component.

According to some examples, the step of estimating at least one outer diameter comprises estimating at least two outer diameters, each based on a lateral width determined at a different axial position.

According to another aspect of the inventions, there is provided a computing system comprising a control circuitry a memory communicatively coupled to the control circuitry and storing executable instructions that, when executed by the control circuitry, cause the control circuitry to perform operations comprising that include receiving an image, acquired by an imagine device, of a prosthetic valve. The operations further include analyzing the image to determine at least one lateral width. The operations further include analyzing the image to identify a constant-length structural component.

The operations further include retrieving a length of the constant-length structural component and associate the length with the identified constant-length structural component. The operations further include estimating at least one outer diameter of the prosthetic valve, based at least in part on the at least one lateral width determined at the axial position of the estimated outer diameter, and the length of the constant-length structural component. The operations further include outputting an indication of the estimated at least one outer diameter.

According to some examples, analyzing the image to determine at least one lateral width further comprises identifying structural components of the prosthetic valve, prior to determining at least one lateral width.

According to some examples, identifying structural components comprises identification of at least one cell, wherein the at least one lateral width extends between two laterally aligned junctions of the same cell.

According to some examples, the at least one lateral width comprises a plurality of lateral widths, each positioned at a different axial position along the length of the prosthetic valve.

According to some examples, identifying structural components further comprises classifying the identified cell as a closed cell or an open cell.

According to some examples, the at least one lateral width extends between two laterally aligned junctions of the same cell.

According to some examples, the identifying structural components comprises identification of at least one cells column.

According to some examples, identifying structural components further comprises classifying the identified cell column as an apical cell column or a non-apical cell column.

According to some examples, the at least one lateral width comprises a plurality of lateral widths, each positioned at a different axial position along the length of the prosthetic valve.

According to some examples, at least two of the plurality of lateral widths are extending between lateral junctions associated with the same cell column.

According to some examples, the at least one identified cell column comprises at least two cell columns, wherein the plurality of lateral widths comprises at least one lateral width extending between lateral junctions of each of the two cell columns.

According to some examples, analyzing the image to determine at least one lateral width further comprises determining at least one opening angle, and wherein the lateral width is calculated from the opening angle and a length of a strut segment.

According to some examples, the opening angle is defined between two intersecting strut segments, and wherein the opening angle is facing the lateral width.

According to some examples, the opening angle is defined between a strut segment and the lateral width.

According to some examples, the operations further comprise analyzing the image to determine at least one vertical height.

According to some examples, the at least one vertical height comprises a plurality of vertical heights, wherein the operations further comprise comparing between the vertical heights and generating data indicative of whether the expansion of the prosthetic valve is non-even.

According to some examples, the constant-length structural component is an outer member of an expansion and locking assembly coupled to a frame of the prosthetic valve.

According to some examples, the constant-length structural component is a strut segment of the prosthetic valve.

According to some examples, estimating at least one outer diameter comprises calculating a diameter of a circumcircle surrounding an internal polygon defined between junctions disposed around the prosthetic valve at a corresponding lateral plane, wherein the length of each of the edges of the internal polygon is the lateral width determined at the axial position of the lateral plane, and wherein the calculation further includes conversion of distances from pixels to length units based at least in part on the length of the constant-length structural component.

According to some examples, the calculation further includes adding a product of thickness of a junction.

According to some examples, the operations further comprise a step of estimating at least one inner diameter by executing the same calculation but without adding a product of the thickness of a junction thereto.

According to some examples, estimating at least one outer diameter comprises estimating at least two outer diameters, each based on a lateral width determined at a different axial position.

According to some examples, estimating at least one outer diameter further comprises estimating at least one outer diameter at an axial position for which a lateral width has not been determined.

According to some examples, the outer diameter at an axial position for which a lateral width has not been determined, is extrapolated from at least two outer diameters estimated from lateral widths determined at axial positions on one side thereof.

According to some examples, the outer diameter at an axial position for which a lateral width has not been determined, is interpolated from at least two outer diameters estimated from lateral widths determined at axial positions on both sides thereof.

According to some examples, the at least one estimated outer diameter is selected from: the inflow diameter, the outflow diameter, and/or the annular diameter.

Certain examples of the present invention may include some, all, or none of the above advantages. Further advantages may be readily apparent to those skilled in the art from the figures, descriptions, and claims included herein. Aspects and examples of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following examples and aspects thereof are described and illustrated in conjunction with systems, tools and methods which are meant to be exemplary and illustrative, but not limiting in scope. In various examples, one or more of the above-described problems have been reduced or eliminated, while other examples are directed to other advantages or improvements.

BRIEF DESCRIPTION OF THE FIGURES

Some examples of the invention are described herein with reference to the accompanying figures. The description, together with the figures, makes apparent to a person having ordinary skill in the art how some examples may be practiced. The figures are for the purpose of illustrative description and no attempt is made to show structural details of an example in more detail than is necessary for a fundamental understanding of the invention. For the sake of clarity, some objects depicted in the figures are not to scale.

In the Figures.

DETAILED DESCRIPTION OF SOME EXAMPLES

Figures 1, 2:
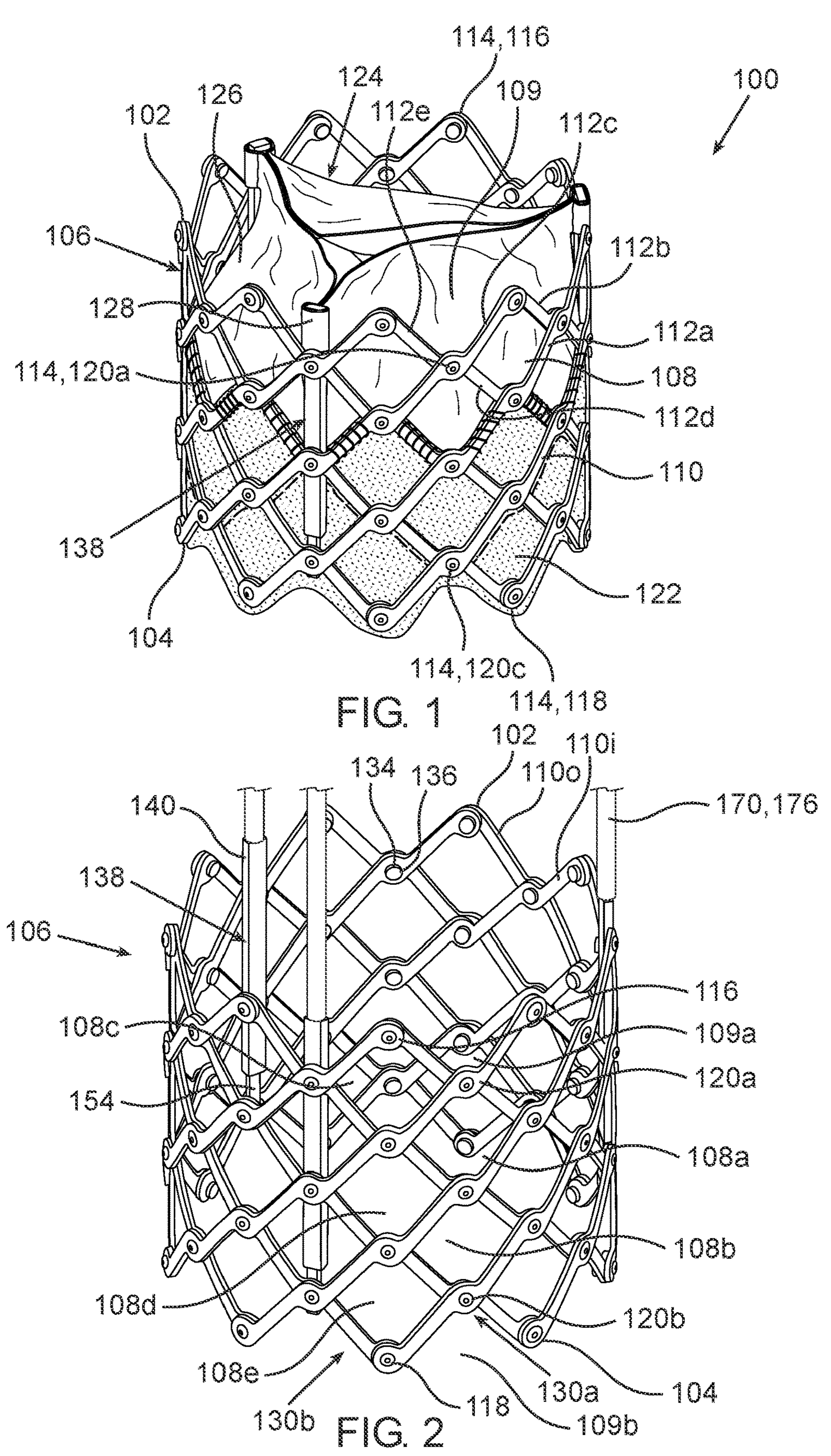
FIGS. 1 and 2 are views in perspective of a mechanically expandable prosthetic valve with and without soft components of the valve, respectively, according to some examples.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

Throughout the figures of the drawings, different superscripts for the same reference numerals are used to denote different examples of the same elements. Examples of the disclosed devices and systems may include any combination of different examples of the same elements. Specifically, any reference to an element without a superscript may refer to any alternative example of the same element denoted with a superscript. In order to avoid undue clutter from having too many reference numbers and lead lines on a particular drawing, some components will be introduced via one or more drawings and not explicitly identified in every subsequent drawing that contains that component.

FIGS. 1 and 2 show perspective views of an exemplary example of a prosthetic valve 100, with and without soft components (such as a skirt and a leaflet assembly), respectively. The term "prosthetic valve", as used herein, refers to any type of a prosthetic valve deliverable to a patient's target site over a catheter, which is radially expandable and compressible between a radially compressed, or crimped, state, and a radially expanded state. Thus, a prosthetic valve 100 can be crimped or retained by a delivery apparatus (not shown) in a compressed state during delivery, and then expanded to the expanded state once the prosthetic valve 100 reaches the implantation site. The expanded state may include a range of diameters to which the valve may expand, between the compressed state and a maximal diameter reached at a fully expanded state. Thus, a plurality of partially expanded states may relate to any expansion diameter between radially compressed or crimped state, and maximally expanded state. A prosthetic valve 100 of the current disclosure may include any prosthetic valve configured to be mounted within the native aortic valve, the native mitral valve, the native pulmonary valve, and the native tricuspid valve.

The term "plurality", as used herein, means more than one.

According to some examples, the prosthetic valve 100 is a mechanically expandable valve. Mechanically expandable valves are a category of prosthetic valves that rely on a mechanical actuation mechanism for expansion. The mechanical actuation mechanism usually includes a plurality of expansion and locking assemblies, releasably coupled to respective actuation assemblies of a delivery apparatus, controlled via a handle for actuating the expansion and locking assemblies to expand the prosthetic valve to a desired diameter.

The prosthetic valve 100 can comprise an inflow end 104 and an outflow end 102. In some instances, the outflow end 102 is the distal end of the prosthetic valve 100, and the inflow end 104 is the proximal end of the prosthetic valve 100. Alternatively, depending for example on the delivery approach of the valve, the outflow end can be the proximal end of the prosthetic valve, and the inflow end can be the distal end of the prosthetic valve.

The term "proximal", as used herein, generally refers to a position, direction, or portion of any device or a component of a device, which is closer to the user and further away from the implantation site.

The term "distal", as used herein, generally refers to a position, direction, or portion of any device or a component of a device, which is further away from the user and closer to the implantation site.

The term "outflow", as used herein, refers to a region of the prosthetic valve through which the blood flows through and out of the valve 100.

The term "inflow", as used herein, refers to a region of the prosthetic valve through which the blood flows into the valve 100.

The valve 100 comprises an annular frame 106 movable between a radially compressed configuration and a radially expanded configuration, and a leaflet assembly 124 mounted within the frame 106. The frame 106 can be made of various suitable materials, including plastically-deformable materials such as, but not limited to, stainless steel, a nickel based alloy (e.g., a cobalt-chromium or a nickel-cobalt-chromium alloy such as MP35N alloy), polymers, or combinations thereof. According to some examples, the struts 110 are arranged in a lattice-type pattern. In the example illustrated in FIG. 1-2, the struts 110 are positioned diagonally, or offset at an angle relative to, and radially offset from, the central axis of the valve 100, when the valve 100 is in an expanded state. It will be clear that the struts 110 can be offset by other angles than those shown in FIGS. 1-2, such as being oriented substantially parallel to the longitudinal axis of the valve 100.

According to some examples, the struts 110 are pivotably coupled to each other at junctions 114. In the exemplary example shown in FIGS. 1-2, the end portions of the struts 110 are forming apices 116 at the outflow end 102 and apices 118 at the inflow end 104. The struts 110 can be coupled to each other at additional non-apical junctions 120 formed between the outflow apices 116 and the inflow apices 118. The outflow apices 116, inflow apices 118 and non-apical junction 120, constitute specific types of junctions 114.

Each strut 110 can include strut segments 112 defined between consecutive junctions 114. The junctions 114 can be equally spaced apart from each other along the length of each strut 110, thereby defining a plurality of strut segments 112 having equal lengths. Frame 106 may comprise openings or apertures 134 at the regions of junctions 114. Respective hinges can be included at locations where the apertures 134 of struts 110 overlap each other, via fasteners such as rivets or pins 136, which extend through the apertures. The hinges or pins 136 can allow the struts 110 to pivot relative to one another as the frame 106 is radially expanded or compressed.

In alternative examples, the struts are not coupled to each other via respective hinges, but are otherwise pivotable or bendable relative to each other, so as to permit frame expansion or compression. For example, the frame can be formed from a single piece of material, such as a metal tube, via various processes such as, but not limited to, laser cutting, electroforming, and/or physical vapor deposition, while retaining the ability to collapse/expand radially in the absence of hinges and like.

The frame 106 further comprises a plurality of cells 108, defined between intersecting portions of struts 110. The shape of each cell 108, and the angle between intersecting portions of struts 110 defining the cell borders, vary during expansion or compression of the prosthetic valve 100. An example of a diamond-shaped cell 108 is shown in FIG. 1, defined between strut segments 112*a*, 112*b*, 112*c* and 112*d*. Further details regarding the construction of the frame and the prosthetic valve are described in U.S. Publication Nos. 2018/0153689; 2018/0344456; 2019/0060057 all of which are incorporated herein by reference.

The valve 100 can include a plurality of cell columns 130 formed around the circumference of the frame 106, as shown in FIG. 2. The cell columns 130 can include alternating non-apical columns, such as column 130*a* including cells 108*a* and 108*b* defined between non-apical junctions 120*a* and 120*c*, and apical columns, such as column 130*b* including cells 108*c*, 108*d* and 108*e* defined between apices 116 and 118. Thus, each non-apical cell column 130 can be bound between two neighboring apical cell columns 130, while each apical cell column 130 can be bound between two neighboring non-apical cell columns 130.

A cell column 130 can include closed cells 108 as well as open cells 109. Closed cells 108 are defined by four strut segments, such as segments 112*a*, 112*b*, 112*c* and 112*d* shown in FIG. 1, while open cells 109 are bound only by two strut segment 112, for example between two apical junctions and a non-apical junction. The example of column 130*b* in FIG. 2 includes three closed cells 108*c*, 108*d* and 108*e*. The example of column 130*a* includes two closed cells 108*a* and 108*b*, and two open cells 109*a* and 109*b*. Open cell 109*a* in the illustrated example is defined above cell 108*a*, between two outflow apices 116 and a non-apical proximal-most junction 120*a* disposed therebetween. Open cell 109*b* in the illustrated example is defined below cell 108*b*, between two inflow apices 118 and a non-apical distal-most junction 120*c* disposed therebetween.

The leaflet assembly 124 comprises a plurality of leaflets 126 (e.g., three leaflets), positioned at least partially within the frame 106, and configured to regulate flow of blood through the prosthetic valve 100 from the inflow end 104 to the outflow end 102. While three leaflets 126 arranged to collapse in a tricuspid arrangement similar to the native aortic valve, are shown in the exemplary example illustrated in FIG. 1A, it will be clear that a prosthetic valve 100 can include any other number of leaflets 126, such as two leaflets configured to collapse in a bicuspid arrangement similar to the native mitral valve, or more than three leaflets, depending upon the particular application. The leaflets 126 are made of a flexible material, derived from biological materials (e.g., bovine pericardium or pericardium from other sources), bio-compatible synthetic materials, or other suitable materials as known in the art and described, for example, in U.S. Pat. Nos. 6,730,118, 6,767,362 and 6,908,481, which are incorporated by reference herein.

The leaflets 126 may be coupled to the frame 106 via commissures 128, either directly or attached to other structural elements connected to the frame 106 or embedded therein, such as commissure posts. Further details regarding prosthetic valves, including the manner in which leaflets may be mounted to their frames, are described in U.S. Pat. Nos. 7,393,360, 7,510,575, 7,993,394 and 8,252,202, and U.S. Patent Application No. 62/614,299, all of which are incorporated herein by reference.

According to some examples, the prosthetic valve may further comprise at least one skirt or sealing member. An inner skirt 122 can be mounted on the inner surface of the frame 106, configured to function, for example, as a sealing member to prevent or decrease perivalvular leakage. An inner skirt 122 can further function as an anchoring region for the leaflets 126 to the frame 106, and/or function to protect the leaflets 126 against damage which may be caused by contact with the frame 106, for example during valve crimping or during working cycles of the prosthetic valve 100. Additionally, or alternatively, the prosthetic valve 100 can comprise an outer skirt (not shown) mounted on the outer surface of the frame 106, configure to function, for example, as a sealing member retained between the frame 106 and the surrounding tissue of the native annulus against which the prosthetic valve is mounted, thereby reducing risk of paravalvular leakage past the prosthetic valve 100. Any of the inner skirt 122 and/or outer skirt can be made of various suitable biocompatible materials, such as, but not limited to, various synthetic materials (e.g., PET) or natural tissue (e.g. pericardial tissue).

According to some examples, a prosthetic valve 100 comprises a plurality of expansion and locking assemblies 138, configured to facilitate expansion of the valve 100, and in some instances, to lock the valve 100 at an expanded state, preventing unintentional recompression thereof. Although FIGS. 1-2 illustrate three expansion and locking assemblies 138, mounted to the frame 106, and optionally equally spaced from each other around an inner surface thereof, it should be clear that a different number of expansion and locking assemblies 138 may be utilized, that the expansion and locking assemblies 138 can be mounted to the frame around its outer surface, and that the circumferential spacing between expansion and locking assemblies 138 can be unequal.

The prosthetic valve 100 can be delivered to the site of implantation via a delivery assembly (not shown) carrying the valve 100 in a radially compressed or crimped state, toward the target site, to be mounted against the native anatomy, by expanding the valve 100 via a mechanical expansion mechanism, as will be elaborated below. The delivery assembly can include a delivery apparatus that includes a handle and a plurality of actuation assemblies 170 extending from the handle through a delivery shaft (not shown). FIG. 2 shows three actuation assemblies 170 coupled to three expansion and locking assemblies 138. The actuation assemblies 170 can generally include actuators 172 (visible, for example, in FIGS. 3A-4C) releasably coupled at their distal ends to respective expansion and locking assemblies 138 of the valve 100, and sleeves 176 disposed around the respective actuators 172. Each actuator 172 may be axially movable relative to the sleeve 176 covering it.

Figures 3A, 3B, 3C:
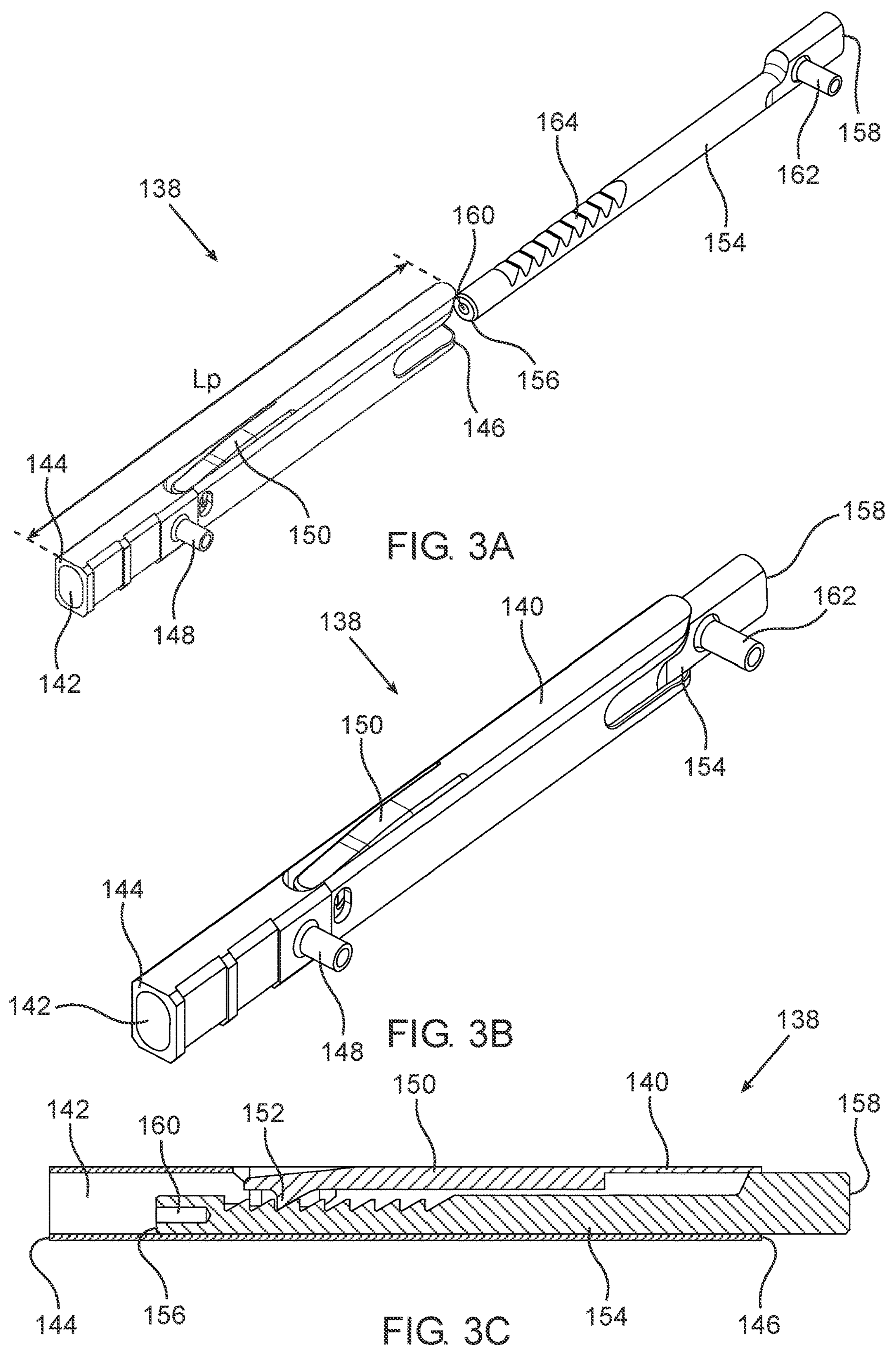
FIGS. 3A-3C show an exploded view in perspective, an assembled view in perspective, and a cross-sectional side view, respectively, of an expansion and locking assembly, according to some examples.

FIGS. 3A, 3B and 3C show an exploded view in perspective, and assembled view in perspective, and a cross-sectional side view, respectively, of an expansion and locking assembly 138 according to some examples. The expansion and locking assembly 138 may include an outer member 140 defining an outer member lumen 142, secured to a component of the valve 100, such as the frame 106, at a first location, and an inner member 154 secured to a component of the 100 114, such as the frame 106, at a second location, axially spaced from the first location.

The inner member 154 extends between an inner member proximal end portion 156 and an inner member distal end portion 158. The inner member 154 comprises an inner member coupling extension 162 extending from its distal end portion 158, which may be formed as a pin extending radially outward from the distal end portion 158, configured to be received within respective openings or apertures 134 of struts 110 intersecting at a junction 114. The inner member 154 may further comprise a linear rack having a plurality of ratcheting teeth 164 along at least a portion of its length. According to some examples, inner member 154 further comprises a plurality of ratcheting teeth 164 along a portion of its outer surface.

The outer member 140 comprises an outer member proximal end portion 144 defining a proximal opening of its lumen 142, and an outer member distal end portion 146 defining a distal opening of its lumen 142. The outer member 140 can further comprise an outer member coupling extension 148 extending from its proximal end portion 144, which may be formed as a pin extending radially outward from the external surface of the proximal end portion 144, configured to be received within respective openings or apertures 134 of struts 110 intersecting at a junction 114.

The outer member 140 can further comprise a spring biased arm 150, attached to or extending from one sidewall of the outer member 140, and having a tooth or pawl 152 at its opposite end, biased inward toward the inner member 154 when disposed within the outer member lumen 142.

At least one of the inner or outer member 154 or 140, respectively, is axially movable relative to its counterpart. The expansion and locking assembly 138 in the illustrated example, comprises a ratchet mechanism or a ratchet assembly, wherein the pawl 152 is configured to engage with the teeth 164 of the inner member 154. The spring-biased arm 150 can comprise an elongate body terminating in a pawl 152 in the form of a locking tooth, configured to engage the ratcheting teeth 164 of the inner member 154. The pawl 152 can have a shape that is complimentary to the shape of the teeth 164, such that the pawl 152 allows sliding movement of the inner member 154 in one direction relative to the spring-biased arm 150 (e.g., a proximally oriented direction) and resists sliding movement of the inner member 154 in the opposite direction (e.g., a distally oriented direction) when the pawl 152 is in engagement with one of the teeth 164.

The arm 150 can be biased inwardly such that the pawl 152 is resiliently retained in a position engaging one of the teeth 164 of the inner member 154. In the illustrated example, the spring-biased arm 150 is configured as a leaf spring. In some examples, the spring-biased arm 150 can be integrally formed with the outer member 140, in other examples, the spring-biased arm 150 can be separately formed and subsequently coupled to the outer member 140. The biased configuration of the arm 150 ensures that under normal operation, the pawl 152 stay's engaged with the teeth 164 of the inner member 154.

The spring biased arm 150 can be formed of a flexible or resilient portion of the outer member 140 that extends over and contacts, via its pawl 152, an opposing side of the outer surface of the inner member 154. According to some examples, the spring biased arm 150 can be in the form of a leaf spring that can be integrally formed with the outer member 140 or separately formed and subsequently connected to the outer member 140. The spring biased arm 150 is configured to apply a biasing force against the outer surface of the inner member 154, so as to ensure that under normal operation, the pawl 152 stays engaged with the ratcheting teeth 164 of the inner member 154.

A mechanically expandable prosthetic valve 100 may be releasably attachable to at least one actuation assembly 170, and preferably a plurality of actuation assemblies 170, matching the number of expansion and locking assemblies

138. In some examples, the prosthetic valve 100 comprises three expansion and locking assemblies 138, and the delivery apparatus comprises three actuation assemblies 170. The actuator 172 and the sleeve 176 can be movable longitudinally relative to each other in a telescoping manner to radially expand and contract the frame 106, as further described in U.S. Publication Nos. 2018/0153689, 2018/0153689 and 2018/0325665, which are incorporated herein by reference. The actuators 172 can be, for example, wires, cables, rods, or tubes. The sleeves 176 can be, for example, tubes or sheaths having sufficient rigidity such that they can apply a distally directed force to the frame 106 or the outer member 140 without bending or buckling.

The inner member proximal end portion 156 further comprises an inner member threaded bore 160, configured to receive and threadedly engage with a threaded portion of a distal end portion 174 (shown for example in FIG. 4C) of a corresponding actuator 172. FIG. 2 shows a view in perspective of a valve 100 in an expanded state, having its expansion and locking assemblies 138 connected to actuators 172 (hidden from view within the sleeves 176). When actuators 172 are threaded into the inner members 154, axial movement of the actuators 172 causes axial movement of the inner members 154 in the same direction.

Figure 4A:
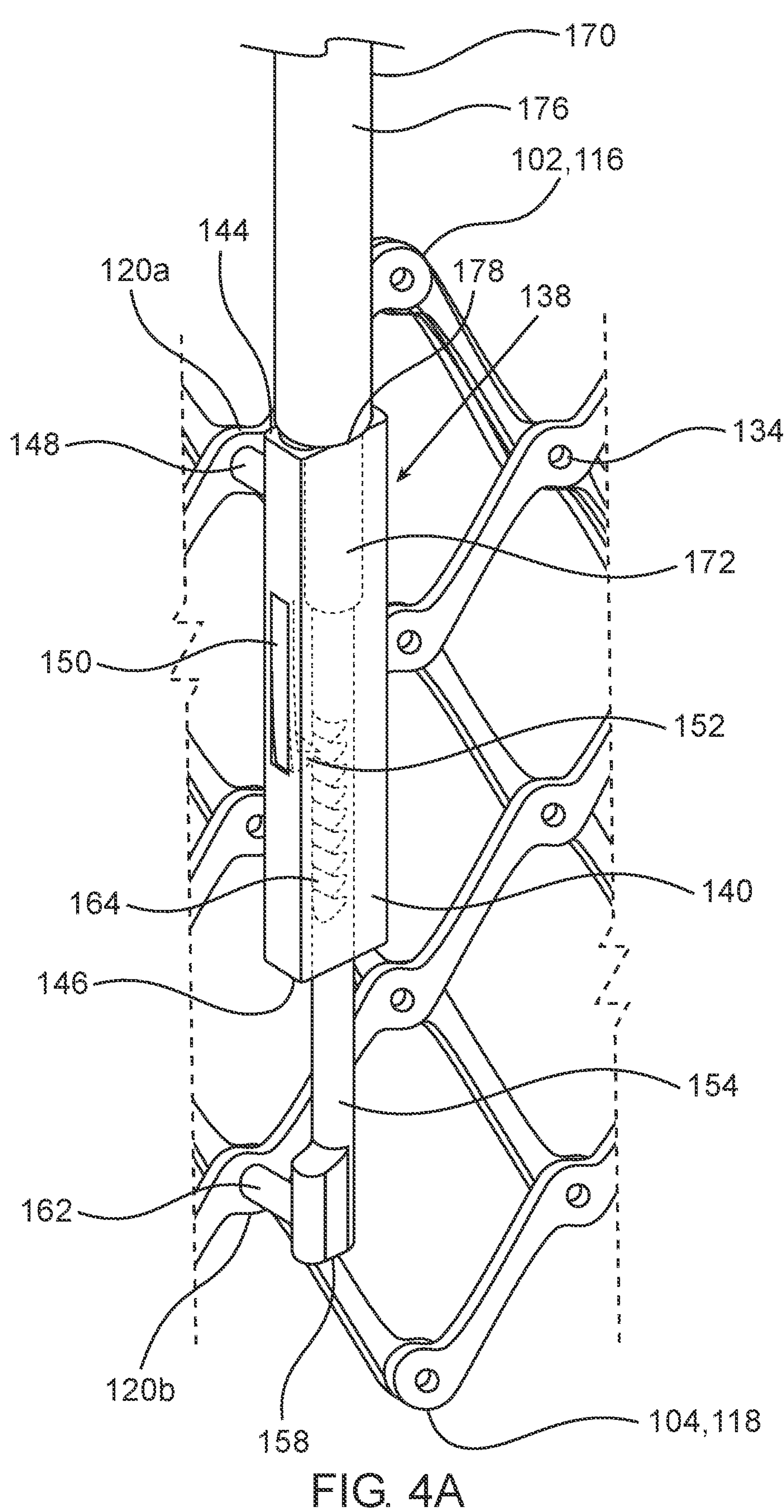
FIGS. 4A-4C show stages of actuating an expansion and locking assembly by an actuation assembly to expand a prosthetic valve from a radially compressed configuration to a radially expanded configuration, according to some examples.
Figure 4B:
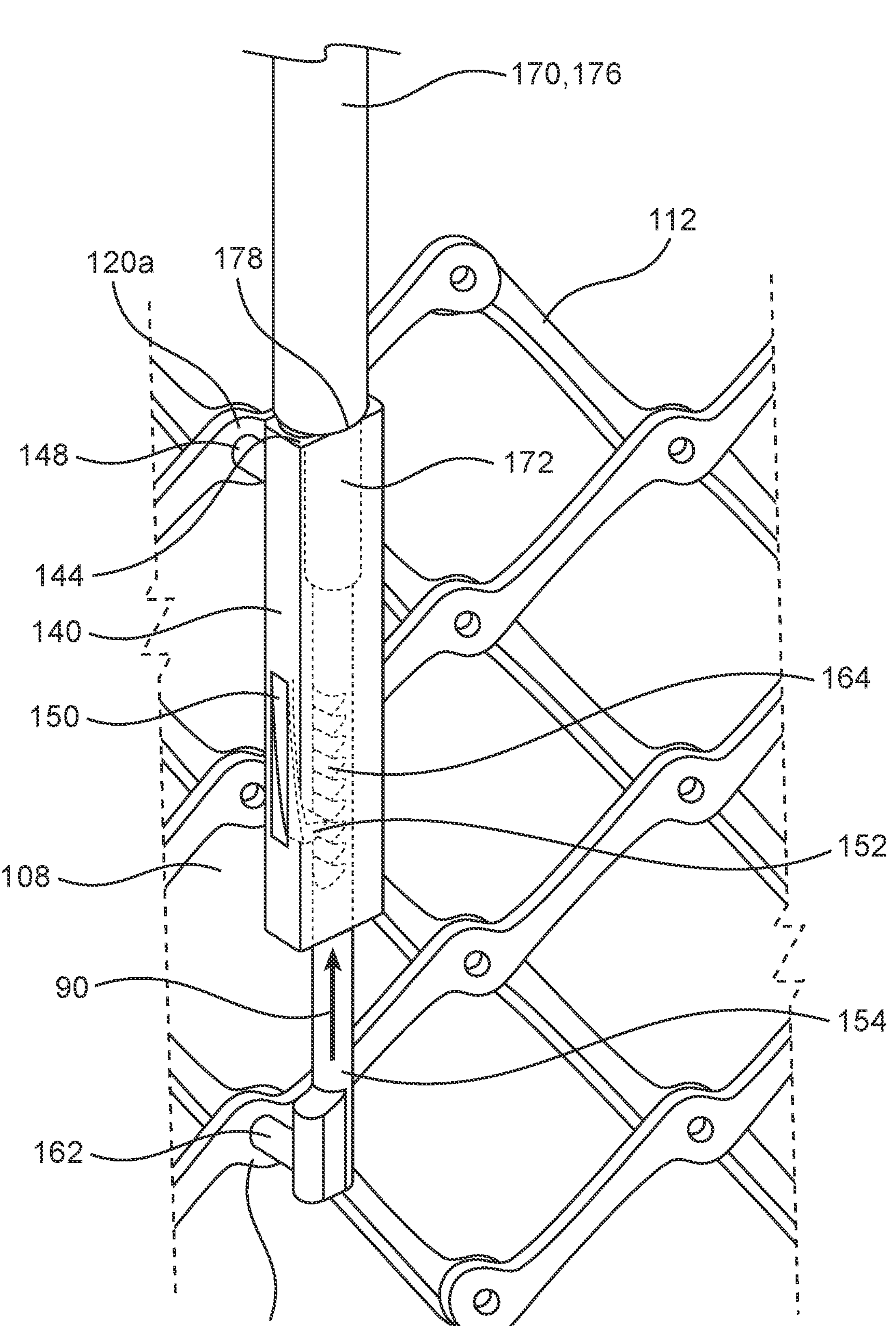
Figure 4C:
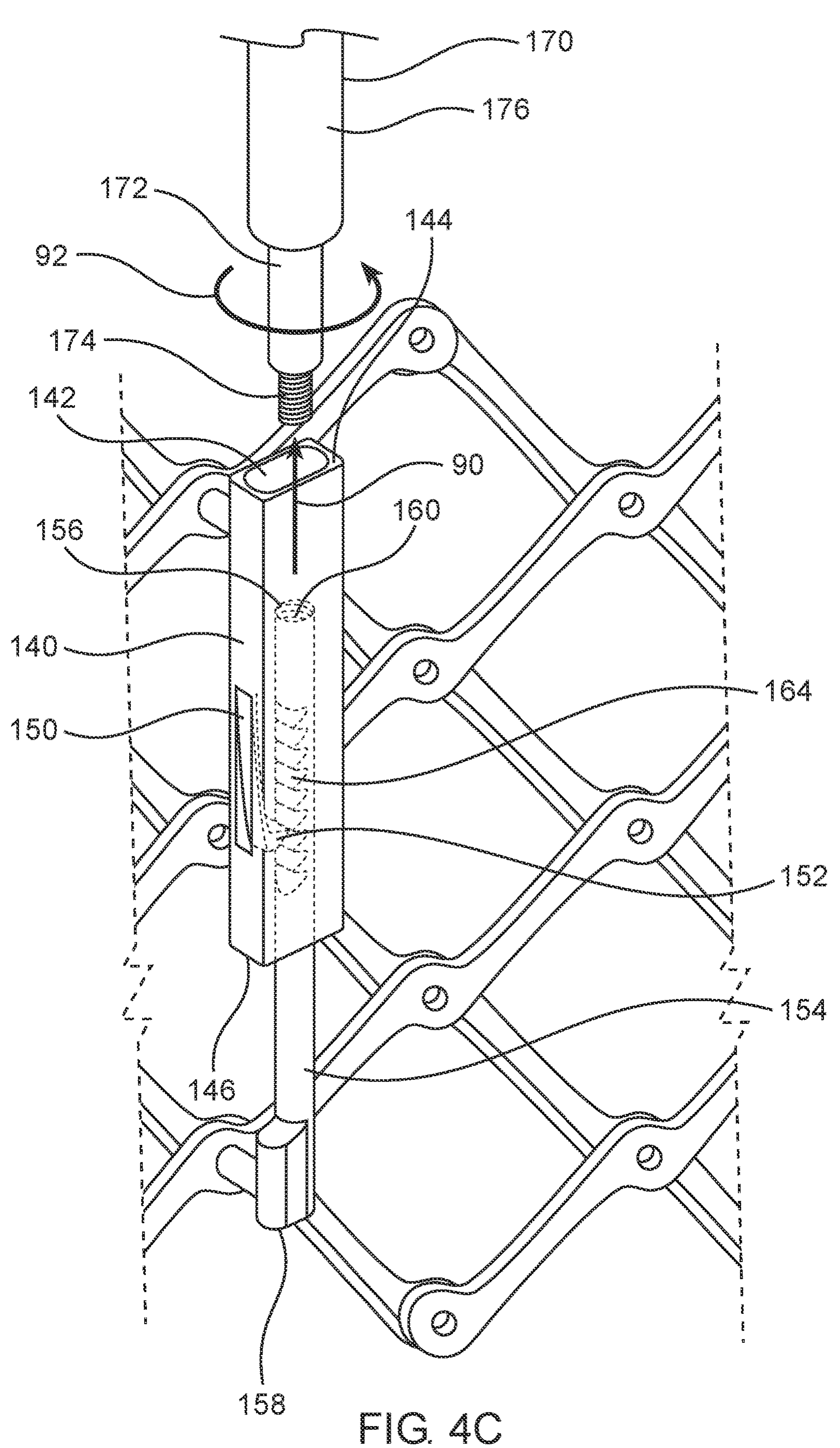

According to some examples, the actuation assemblies 170 are configured to releasably couple to the prosthetic valve 100, and to move the prosthetic valve 100 between the radially compressed and the radially expanded configurations. FIGS. 4A-4C illustrate a non-binding configuration representing actuation of the expansion and locking assemblies 138 via the actuation assemblies 170 to expand the prosthetic valve 100 from a radially compressed configuration to a radially expanded configuration.

FIG. 4A shows an expansion and locking assembly 138, having an outer member 140, secured to the frame 106 at a first location, and an inner member 154 secured to the frame 106 at a second location. According to some examples, the first location can be positioned at or adjacent to the outflow end 102, and the second location can be positioned at or adjacent to the inflow end 104. In the illustrated example, the outer member 140 is secured to a non-apical proximal-most junction 120*a* which is distal to the outflow apices 116 or the outflow end 102, via outer member coupling extension 148, and the inner member 154 is secured to a non-apical distal-most junction 120*c* which is proximal to the inflow apices 118 or the inflow end 104, via inner member coupling extension 162. A proximal portion of the inner member 154 extends, through the distal opening of the outer member distal end 146, into the outer member lumen 142.

It is to be understood that while the illustrated examples are for an expansion and locking assembly 138 secured to a non-apical proximal-most junction 120*a* serving as the first location, and to a non-apical distal-most junction 120*c* serving as the second location, in other implementations, the expansion and locking assembly 138 can be secured to other junctions. For example, the expansion and locking assembly can be secured to an outflow apex 116 via the outer member coupling extension 148, serving as the first location, and to an opposing inflow apex 118 along the same cell column 130, via the inner member coupling extension 162, serving as the second location.

The expansion and locking assembly 138 is shown in FIG. 4A in a radially compressed state of the valve 100, wherein the outflow and inflow apices 116 and 118, respectively, are relatively distanced apart from each other along the axial direction, and the inner member proximal end portion 156 is positioned distal to the outer member proximal end portion 144.

As further shown in FIG. 4A, the actuator distal end portion 174 is threadedly engaged with the inner member threaded bore 160. According to some examples, as shown in FIGS. 4A-4C, the actuator distal end portion 174 includes external threads, configured to engage with internal threads of the inner member threaded bore 160. According to alternative examples, an inner member may include a proximal extension provided with external threads, configured to be received in and engage with internal threads of a distal bore formed within the actuator (examples not shown).

The sleeve 176 surrounds the actuator 172 and may be connected to the handle of a delivery apparatus. The sleeve 176 and the outer member 140 are sized such that the distal lip 178 of the sleeve 176 can abut or engage the outer member proximal end 144, such that the outer member 140 is prevented from moving proximally beyond the sleeve 176.

In order to radially expand the frame 106, and therefore the valve 100, the sleeve 176 can be held firmly against the outer member 140. The actuator 172 can then be pulled in a proximally oriented direction 90, as shown in FIG. 4B. Because the sleeve 176 is being held against the outer member 140, which is connected to the frame 106 at the first location, the outflow end 102 of the frame 106 is prevented from moving relative to the sleeve 176. As such, movement of the actuator 172 in a proximally oriented direction 90 can cause movement of the inner member 154 in the same direction, thereby causing the frame 106 to foreshorten axially and expand radially.

More specifically, as shown for example in FIG. 4B, the inner member coupling extension 162 extends through apertures 134 in two struts 110 interconnected at a non-apical distal junction 120*c*, while the outer member coupling extension 148 extends through aperture 134 in two struts 110 interconnected at a non-apical proximal junction 120*a*. As such, when the inner member 154 is moved axially, for example in a proximally oriented direction 90, within the outer member lumen 142, the inner member coupling extension 162 moves along with the inner member 154, thereby causing the portion to which the inner member coupling extension 162 is attached to move axially as well, which in turn causes the frame 106 to foreshorten axially and expand radially.

The struts 110 to which the inner member coupling extension 162 is connected are free to pivot relative to the coupling extension 162 and to one another as the frame 106 is expanded or compressed. In this manner, the inner member coupling extension 162 serves as a fastener that forms a pivotable connection between those struts 110. Similarly, struts 110 to which the outer member coupling extension 148 is connected are also free to pivot relative to the coupling extension 148 and to one another as the frame 106 is expanded or compressed. In this manner, the outer member coupling extension 148 also serves as a fastener that forms a pivotable connection between those struts 110.

As mentioned above, when the pawl 152 of the spring biased arm 150 is engaged with the ratcheting teeth 164, the inner member 154 can move in one axial direction, such as the proximally oriented direction 90, but cannot move in the opposite axial direction. This ensures that while the pawl 152 is engaged with the ratcheting teeth 164, the frame 106 can radially expand but cannot be radially compressed. Thus, after the prosthetic valve 100 is implanted in the patient, the frame 106 can be expanded to a desired diameter by pulling the actuator 172. In this manner, the actuation mechanism also serves as a locking mechanism of the prosthetic valve 100.

Once the desired diameter of the prosthetic valve 100 is reached, the actuator 172 may be rotated, for example in rotation direction 92, to unscrew the actuator 172 from the inner member 154, as shown in FIG. 4C. This rotation serves to disengage the distal threaded portion 174 of the actuator 172 from the inner member threaded bore 160, enabling the actuation assemblies 170 to be pulled away, and retracted, together with the delivery apparatus, from the patient's body, leaving the prosthetic valve 100 implanted in the patient. The patient's native anatomy, such as the native aortic annulus in the case of transcatheter aortic valve implantation, may exert radial forces against the prosthetic valve 100 that would strive to compress it. However, the engagement between the pawl 152 of the spring biased arm 150 and the ratcheting teeth 164 of the inner member 154 prevents such forces from compressing the frame 106, thereby ensuring that the frame 106 remains locked in the desired radially expanded state.

Thus, the prosthetic valve 100 is radially expandable from the radially compressed state shown in FIG. 4A to the radially expanded state shown in FIG. 4B upon actuating the expansion and locking assemblies 138, wherein such actuation includes approximating the second locations to the first locations of the valve 100. The prosthetic valve 100 is further releasable from the delivery apparatus by decoupling each of the actuation assemblies 170 from each of the corresponding expansion and locking assemblies 138 that were attached thereto.

While the frame 106 is shown above to expand radially outward by axially moving the inner member 154 in a proximally oriented direction 90, relative to the outer member 140, it will be understood that similar frame expansion may be achieved by axially pushing an outer member 140 in a distally oriented direction, relative to an inner member 154.

While a threaded engagement is illustrated and described in the above examples, serving as an optional reversible-attachment mechanism between the actuation assemblies 170 and the inner members 154, it is to be understood that in alternative implementations, other reversible attachment mechanisms may be utilized, configured to enable the inner member 154 to be pulled or pushed by the actuation assemblies 170, while enabling disconnection therebetween in any suitable manner, so as to allow retraction of the delivery apparatus from the patient's body at the end of the implantation procedure. For example, the distal end portion of the actuator can include a magnet, and the inner member bore can include a correspondingly magnetic material into which the distal end portion of the actuator can extend.

While a specific actuation mechanism is described above, utilizing a ratcheting mechanism between the inner and the outer members of the expansion and locking assemblies 138, other mechanisms may be employed to promote relative movement between inner and outer members of actuation assemblies, for example via threaded or other engagement mechanisms. Further details regarding the structure and operation of mechanically expandable valves and delivery system thereof are described in U.S. Pat. No. 9,827,093, U.S. Patent Application Publication Nos. 2019/0060057, 2018/0153689 and 2018/0344456, and U.S. Patent Application Nos. 62/870,372 and 62/776,348, all of which are incorporated herein by reference.

The prosthetic valve 100 can be delivered to the implantation site in a crimped state, wherein the frame 106 can be designed to assume a cylindrical or nearly cylindrical configuration during the crimped state, following a substantially uniform diameter along the length of the prosthetic valve. In some configurations, the frame is configured to assume a nearly cylindrical configuration during expansion as well, resulting in a substantially uniform diameter of the frame 106 between the inflow end 104 and the outflow end 102 at the expanded configuration.

In alternative designs, the frame may assume a tapering configuration during expansion, assuming a frustoconical shape having a varying diameter between the inflow end 104 and the outflow end 102 at the various expanded configurations, including various partially expanded configurations thereof.

Figure 5A:
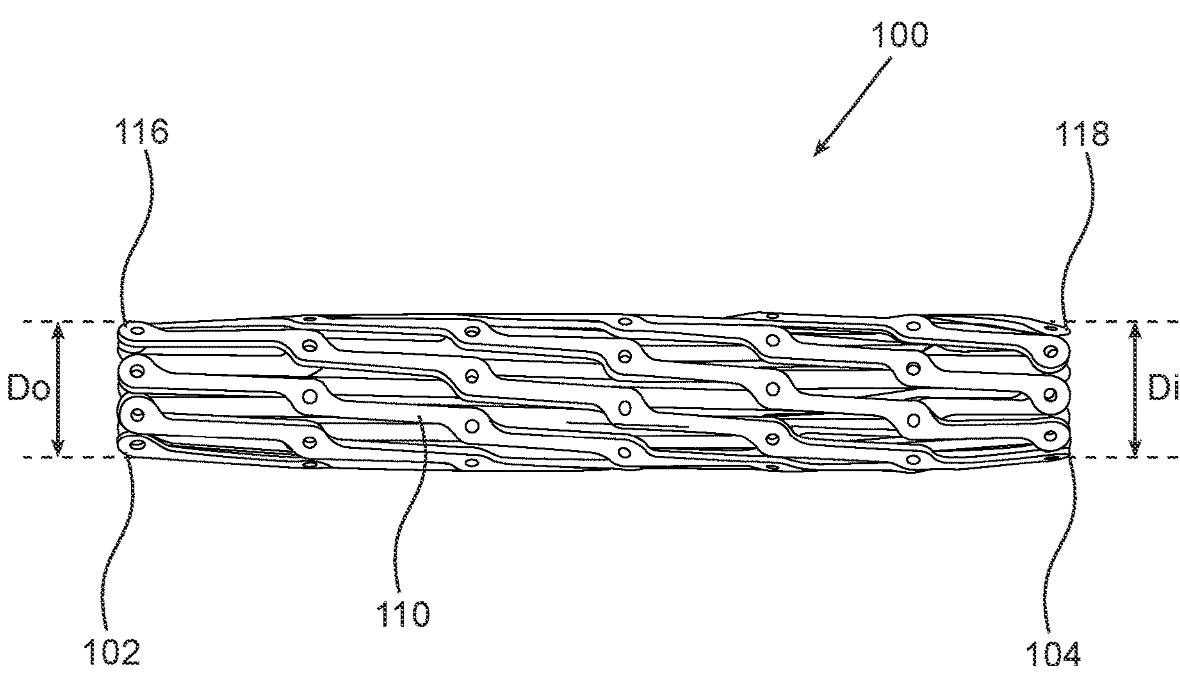
FIGS. 5A-5C show various stages of an example of a prosthetic valve expanded between a crimped configuration and a fully expanded configuration.
Figure 5B:
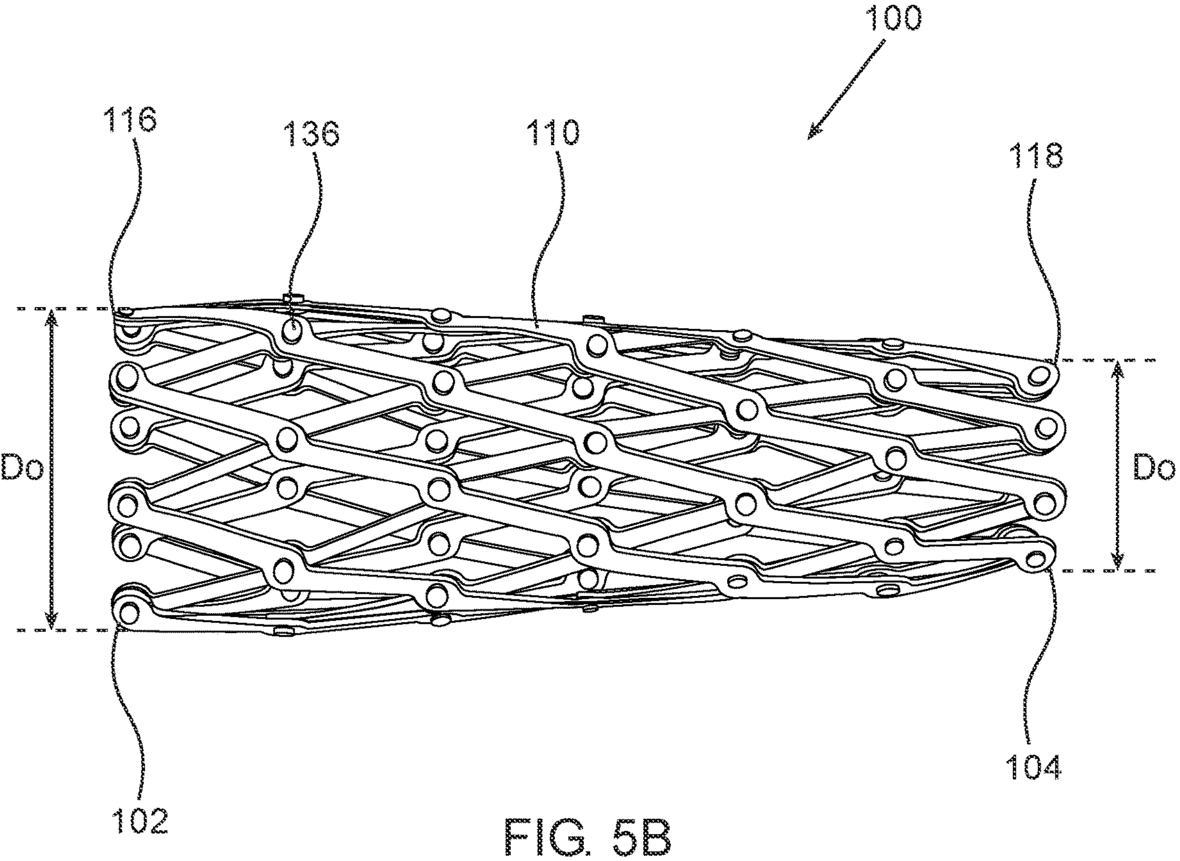
Figure 5C:
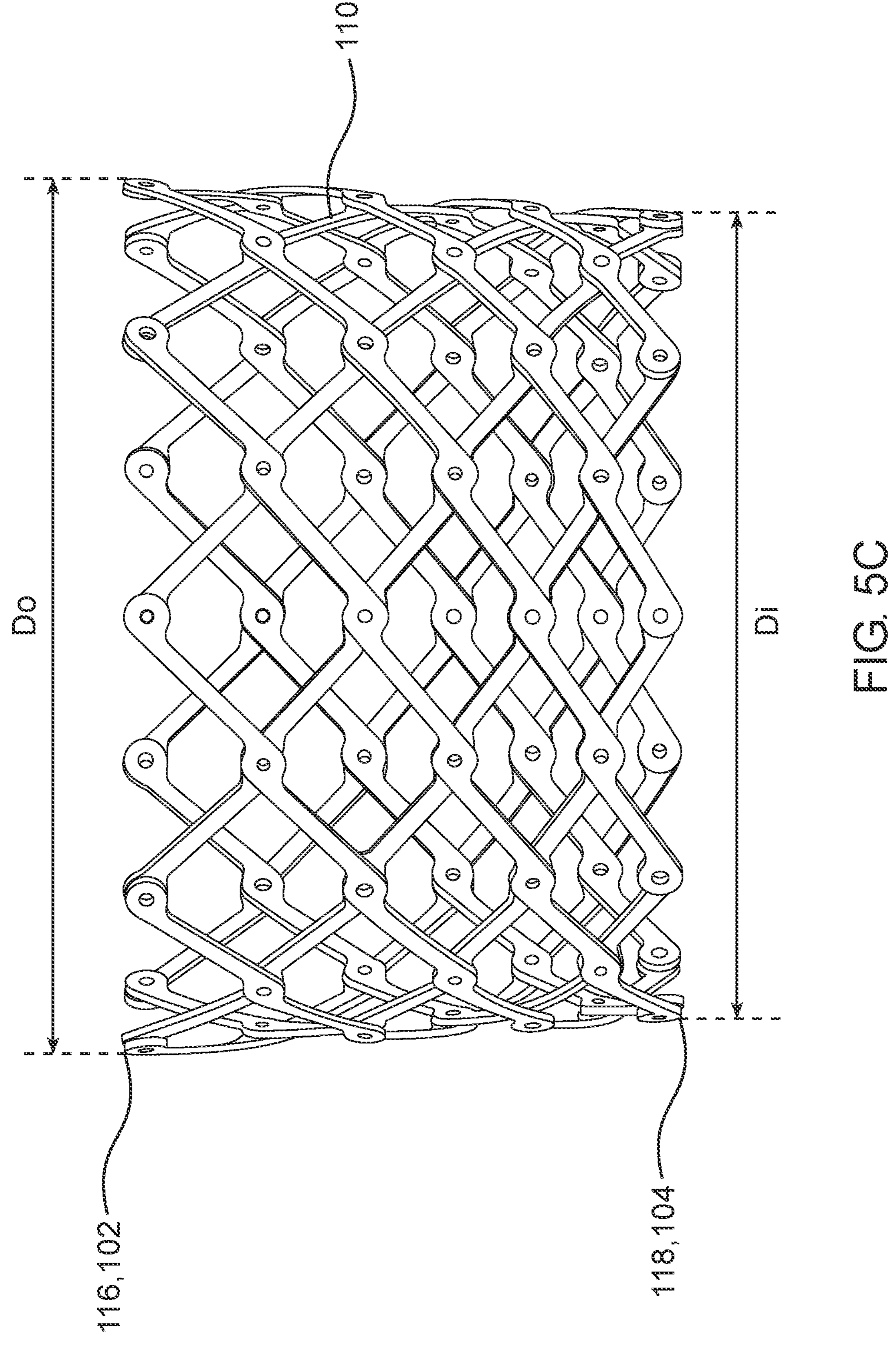

FIGS. 5A-5C show various stages of an example of a frame 106 expanded between a crimped configuration and a fully expanded configuration. The inflow end 104 has an inflow diameter Di and the outflow end 102 has an outflow diameter Do. The frame 106 of a prosthetic valve 100 is shown throughout FIGS. 5A-5C without expansion and locking assemblies for ease of illustration.

FIG. 5A shows a crimped configuration of the prosthetic valve 100, wherein the outflow diameter Do may be substantially equal to the inflow diameter Di. In some cases, the outflow diameter Do may be even narrower than the inflow diameter Do, so as to facilitate advancement of the prosthetic valve 100 through the patient's vasculature during delivery to the implantation site.

FIG. 5B shows an intermediate, partially expanded configuration of the prosthetic valve 100, wherein the valve 100 can assume a frustoconical shape having the outflow diameter Do larger than the inflow diameter Di. FIG. 5C shows the prosthetic valve further expanded, for example to a maximally expanded configuration, wherein the outflow diameter Do in this configuration is larger than the outflow diameter Do in the partially expanded configuration shown in FIG. 5B, and wherein the inflow diameter Di in this configuration is larger than the inflow diameter Di in the partially expanded configuration shown in FIG. 5B.

While the outflow diameter Do remains larger than the inflow diameter Di in the fully expanded configuration shown in FIG. 5C, the ratio of the outer diameter to the inner diameter Do/Di, or the absolute difference between both diameters Do−Di, may be different between the fully expanded configuration shown in FIG. 5C and the partially expanded configuration shown in FIG. 5B.

Potential advantages that can be associated with the frustoconical deployed shape of the frame 106 in which the outflow diameter Do is greater than the inflow diameter Di are that the wider outflow end 102 can provide for improved anchoring of the prosthetic valve 100 at the level of the native leaflets and/or annulus, and can provide improved hydrodynamic function. The smaller inflow diameter Di can space the frame 106 away from the His bundle, reducing the risk of electrical conduction abnormalities and rupture of the native valve annulus.

Figure 6:
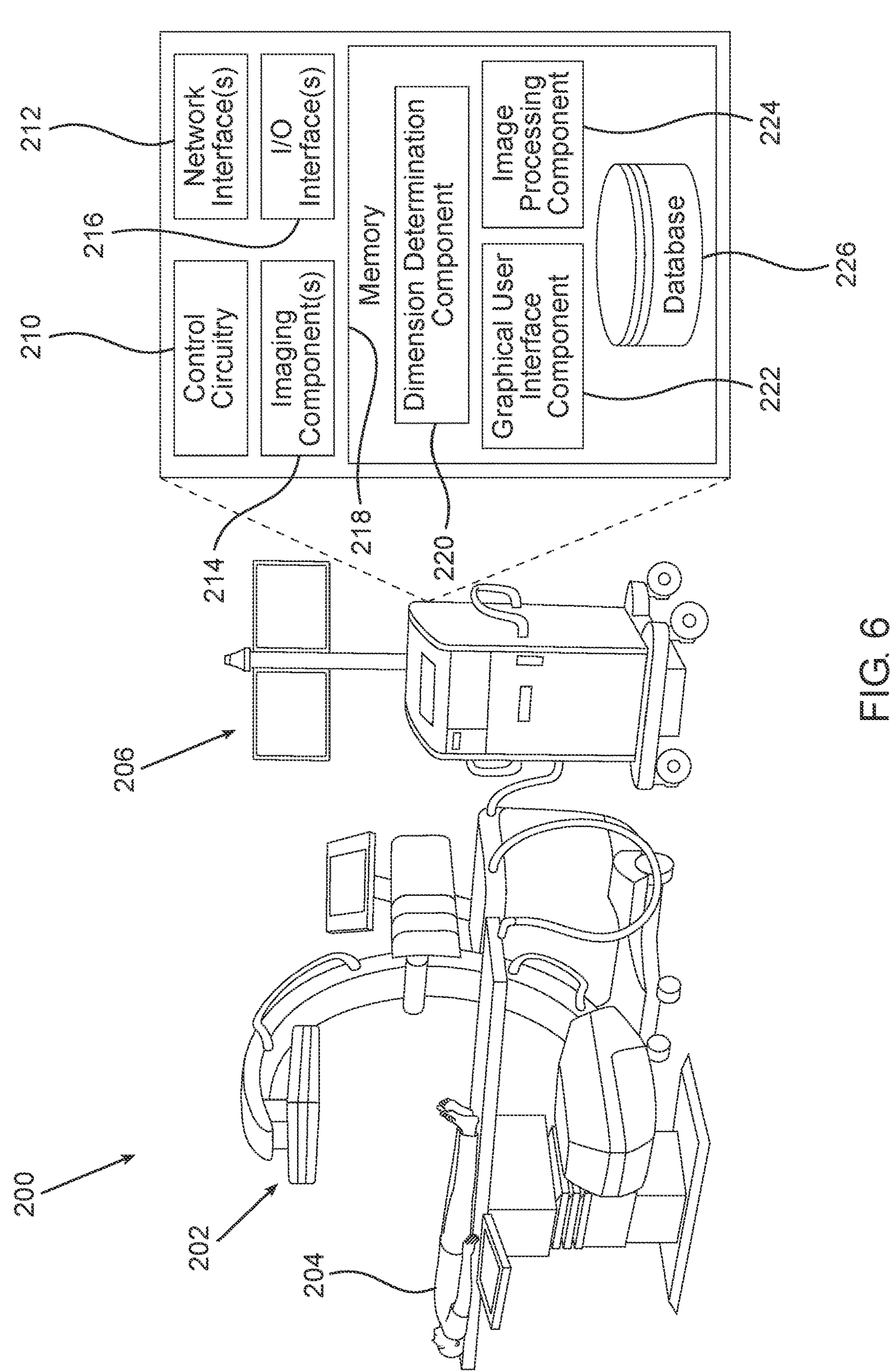
FIG. 6 shows an example architecture for estimating valve diameters in real-time during valve expansion procedures, according to some examples.

Reference is now made to FIG. 6, illustrating an example architecture 200 for estimating valve diameters in real-time during valve expansion procedures, based on an analysis of one or more images acquired during valve expansion at the site of implantation. The architecture 200 includes one or more imaging devices 202 (referred to as "the imaging device 202", for ease of discussion) configured to capture/generate one or more images of the prosthetic valve 100 during implantation within a patient 204, and one or more computing systems 206 (referred to as "the computing system 206", for ease of discussion) configured to evaluate one or more images to estimate at least one diameter of the prosthetic valve 100. In some examples, an indication of the estimated at least one diameter is output. As will be described below; the indication of the estimated at least diameter can include: one or more estimated diameters, optionally in SI measurements; and/or an axial profile of the prosthetic valve. The imaging device 202 and the computing system 206 can be configured to communicate via wired or wireless communication appliances, such as to send/receive data including one or more images created by the imaging device 202 and/or other data. The computing system 206 can be configured to receive input from and/or provide output to a user, such as a physician, a technician, a radiologist, and so on. In some examples, the imaging device 202 and the computing system 206 are located at the same facility/environment/location.

The imaging device 202 can be implemented as one or more x-ray devices, ultrasound devices, and/or other types of medical imaging devices. The imaging device 202 can generally be configured to capture/generate one or more images including visual representations of interior anatomy, such as of the organs/tissues/other anatomical features of a patient, and prosthetic devices positioned within the patient's body, such as stents, prosthetic valves and the like. According to some examples, the imaging device 202 is a fluoroscopic imaging device. A fluoroscopy device, as shown in the example illustrated in FIG. 6, can include a fluoroscopy source and a fluoroscopy detector. In some examples, the architecture 200 comprises a fluoroscopy device 202 and a monitor 216. The fluoroscopy source can be positioned over patient 204 so as to obtain a left anterior oblique (LAO) projection of between 30 and 45, such as between 30 and 40, degrees with a 30-degree cranial tilt (for orthogonal projection of the aortic annulus). In some examples, the imaging device 202 includes more than one device, such as a fluoroscopy device used in combination with an ultrasound probe (not shown) for imaging enhancement.

The computing system 206 can be implemented as one or more computing devices, such as one or more desktop computers, laptops computers, servers, smartphones, electronic reader devices, mobile handsets, personal digital assistants, portable navigation devices, portable gaming devices, tablet computers, wearable devices (e.g., a watch, optical head-mounted display, etc.), portable media players, televisions, set-top boxes, computer systems in a vehicle, appliances, cameras, security systems, home-based computer systems, projectors, medical monitors, and so on. In some examples, the one or more computing devices are configured in a cluster, data center, cloud computing environment, or a combination thereof. In some examples, the one or more computing devices are implemented as local resources that are located locally at an environment of the imaging device 202.

As illustrated, the computing system 206 can include one or more of the following components, devices, modules, and/or units (referred to herein as "components"), either separately/individually and/or in combination/collectively: control circuitry 210, one or more network interfaces 212, one or more imaging components 214, one or more I/O interfaces 216, and/or memory 218. Although certain components of the computing system 206 are illustrated in FIG. 6, it should be understood that additional components not shown can be included in examples in accordance with the present disclosure. Furthermore, certain of the illustrated components can be omitted in some examples.

Although the control circuitry 210 is illustrated as a separate component in the diagram of FIG. 6, it should be understood that any or all of the remaining components of the computing system 206 can be embodied at least in part in the control circuitry 210. That is, the control circuitry 210 can include various devices (active and/or passive), semiconductor materials and/or areas, layers, regions, and/or portions thereof, conductors, leads, vias, connections, and/or the like, wherein one or more of the other components of the computing system 206 and/or portion(s) thereof can be formed and/or embodied at least in part in/by such circuitry components/devices. Specifically, any discussion of steps that are performed dimension determination component 220, which is illustrated as a component of memory 218 in FIG. 6 and shown separately from control circuitry 210, may actually be performed by control circuitry 210, wherein any of the memory 218 and/or the dimension determination component 220) can be embodied within the control circuitry 210. Moreover, in some examples, dimension determination component 220 is embodied as a set of instructions (e.g., software commands and algorithms) that are performed by a processor of the control circuitry 210.

The various components of the computing system 206 can be electrically and/or communicatively coupled using certain connectivity circuitry/devices/features, which may or may not be part of the control circuitry 210. For example, the connectivity feature(s) can include one or more printed circuit boards configured to facilitate mounting and/or interconnectivity of at least some of the various components/circuitry of the computing system 206. In some examples, one or more control circuitry 210, the one or more network interfaces 212, the one or more imaging components 214, the one or more I/O interfaces 216, and/or the database/memory 218, can be electrically and/or communicatively coupled to each other.

The one or more network interfaces 212 can be configured to communicate with one or more devices/systems over one or more networks. For example, the one or more network interfaces 212 can send/receive data in a wireless and/or wired manner over a network, such as one or more images captured by the imaging device 202. The networks can include various communication protocols, such as local area networks (LAN), wide area networks (WAN) (e.g., the Internet), personal area networks (PAN), body area networks (BAN), etc. In some examples, the one or more network interfaces 212 can implement a wireless technology such as Bluetooth, Wi-Fi, near field communication (NFC), or the like.

The one or more imaging components 214 can include generators, sensors, detectors, cameras, etc. configured to provide/generate signals/radiation and/or to receive/detect signals/radiation, which can be used to capture/generate one or more images. While shown schematically as part of the computing system 206, which may communicate with the imaging device 202, it is to be understood that the one or more imaging components 214 can be included within the imaging device 202, and that the computing system 206 can be, in some examples, a control system of the imaging device 202 which is interconnected with other components of the imaging device 202.

The one or more I/O components 216 can include a variety of components to receive input and/or provide output, such as to interface with a user. The one or more I/O components 216 can be configured to receive touch, speech, gesture, or any other type of input. Further, the one or more I/O components 216 can be configured to output display data, audio data, haptic feedback data, or any other type of output data. The one or more I/O components 216 can include the one or more displays (sometimes referred to as "one or more display devices"), touchscreens, touch pads, controllers, mice, keyboards, wearable devices (e.g., optical head-mounted display), virtual or augmented reality devices (e.g., head-mounted display), speakers (e.g., configured to output sounds based on audio signals), microphones (e.g., configured to receive sounds and generate audio signals), cameras, and so on. The one or more displays can include one or more liquid-crystal displays (LCD), light-emitting diode (LED) displays, organic LED displays, plasma displays, electronic paper displays, and/or any other type(s) of technology. In some examples, the one or more displays include one or more touchscreens configured to receive input and/or display data.

As illustrated, the memory 218 can include a dimension determination component 220, a graphical user interface component 222, and/or image processing component 224 configured to facilitate various functionality discussed herein. In some examples, one or more of the components 220-224 can include and/or be implemented as one or more executable instructions that, when executed by the control circuitry 210, cause the control circuitry 210 to perform one or more operations. Although many examples are discussed in the context of the components 220-224 including one or more instructions that are executable by the control circuitry 210, any of the components 220-224 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 220-224 are illustrated as being included within the computing system 206, any of the components 220-224 can be implemented at least in part within another device/system, such as the imaging device 202 (e.g., a fluoroscopy device) and/or another device/system. Similarly, any of the other components of the computing system 206 can be implemented at least in part within another device/system.

The dimension determination component 220 can be configured to identify one or more dimension of a prosthetic valve 100. The dimension determination component 220 can evaluate one or more images acquired by the imaging device 202. The evaluation of the one or more acquired images can determine one or more dimensions of a prosthetic valve 100. A dimension of prosthetic valve 100 can include a length of a component of the prosthetic valve 100, a distance between features or components of the prosthetic valve 100, a ratio between lengths of components of the prosthetic valve 100, and/or an angle between components of the prosthetic valve 100. For example, a dimension of prosthetic valve 100 can include a distance between junctions 114 of the prosthetic valve 100, and/or an angle between intersecting strut segments 112. The dimension determination component 220 can store data indicative of such dimensions of the prosthetic valve 100 in a database 226.

In some examples, the dimension determination component 220 can evaluate one or more images acquired by the imaging device 202 (e.g., a fluoroscopy device) to identify structural components of the prosthetic valve 100 that are visible in the acquired image/s, for example, radiopaque structural components of the prosthetic valve 100, such as struts 110 and strut segments 112 thereof, junctions 114, pins 136 that may extend through apertures 134, as well as components of expansion and locking assemblies 138 such as outer members 140.

In some examples, the dimension determination component 220 can evaluate one or more images acquired by the imaging device 202 (e.g., a fluoroscopy device) to further identify anatomical structures in the vicinity of the implanted prosthetic valve 100, such as walls surrounding a native annulus against which the prosthetic valve 100 is implanted. Such anatomical structures can include, for example, walls of the ascending aorta 12, the aortic annulus 14, the cusps 16, and/or the LVOT 18 (shown, for example, in FIG. 7A).

In some examples, the dimension determination component 220 can evaluate multiple images from different orientations/positions/angles. For example, the dimension determination component 220 can identify one or more dimensions and/or positions of structural components of the prosthetic valve 100 by analyzing a first image from a first orientation/position within a patient and analyzing a second image from a second orientation/position within the patient. In some examples, a position of a structural component of the prosthetic valve 100 can include one or more coordinates of the structural component within a coordinate system/space.

In some examples, one or more dimensions and/or positions of structural components of the prosthetic valve 100 can include a dimensions/position of a visual representation of the structural components of the prosthetic valve 100 and/or dimension of the prosthetic valve 100 in an image, such as a size/length/distance of the visual representation, a color/shading of the visual representation, a position of the visual representation within the image, and so on.

In some examples, the dimension determination component 220 operates in cooperation with the graphical user interface component 222. For example, the graphical user interface component 222 can be configured to provide an interface that includes an image. A user, such as a physician or technician, can view the image and provide input regarding a dimension of the prosthetic valve 100 or position of a structural component of the prosthetic valve 100. In one example, the user can designate a representation in an image as representing a particular structural component, such as strut segment 112, an outer member 140, etc. In another example, a user can designate a first point/location on an image and a second point/location in the image and provide input requesting that a distance be calculated between the first point/location and the second point/location. The user can also provide input to label the distance. In examples, a user can provide input to determine/label any of the dimensions of the prosthetic valve 100. In examples, the dimension determination component 220 can use input provided by a user to evaluate one or more images and/or store data regarding one or more characteristics/positions of one or more dimensions of the prosthetic valve 100 and/or positions of a structural components of the prosthetic valve 100 in the database 226.

Further, in some examples, the dimension determination component 220 operates in cooperation with the image processing component 224 to evaluate an image. For example, the image processing component 224 can perform one or more image processing techniques with one or more images to automatically identify image-based features within the one or more images and/or classify the one or more image-based features as structural components of the prosthetic valve 100. In some examples, the image processing component 224 uses one or more intelligence techniques, such as one or more machine-trained models, to analyze one or more images. In examples, the dimension determination component 220 can use information determined by the image processing component 224 to evaluate one or more images and/or store data regarding one or more characteristics/positions of one or more dimensions of the prosthetic valve 100 and/or positions of a structural components of the prosthetic valve 100 in the database 226.

Data/information generated/determined herein can be used in a variety of manners. In some examples, data regarding one or more dimensions of the prosthetic valve 100 can be used to provide real-time estimates of valve expansion diameter at various regions of the prosthetic valve 100, which in turn can be used to generate instructions/information, such as whether the prosthetic valve 100 should be further expanded, whether an expansion procedure should be halted, or whether re-compressions of the prosthetic valve 100 may be required. In examples, such information can be displayed to a user via a user interface.

As noted above, the database 226 can store one or more images acquired by the imaging device 202, as well as store data regarding dimensions of the prosthetic valve 100 and/or positions of a structural components of the prosthetic valve 100, as well as estimated expansion diameters and optional generated instructions/information. Although the database 226 is illustrated as being included within the computing system 206, in some examples, the database 226 can be implemented elsewhere, such as within a remote resource.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in examples in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with examples of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Figure 7A:
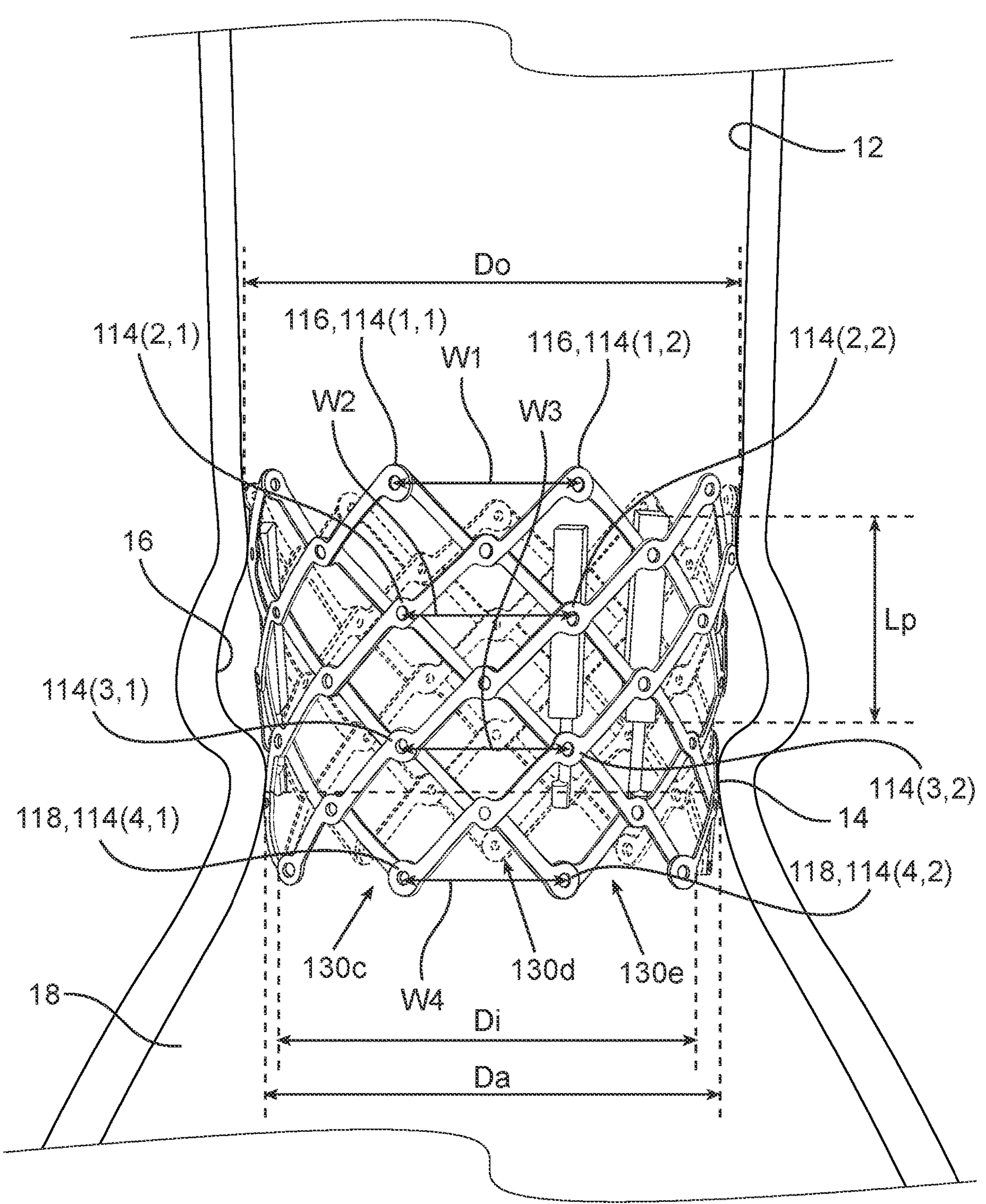
FIGS. 7A-7C show structural components and dimensions of a prosthetic valve that can be identified and determined from acquired images, according to some examples.
Figures 7B, 7C:
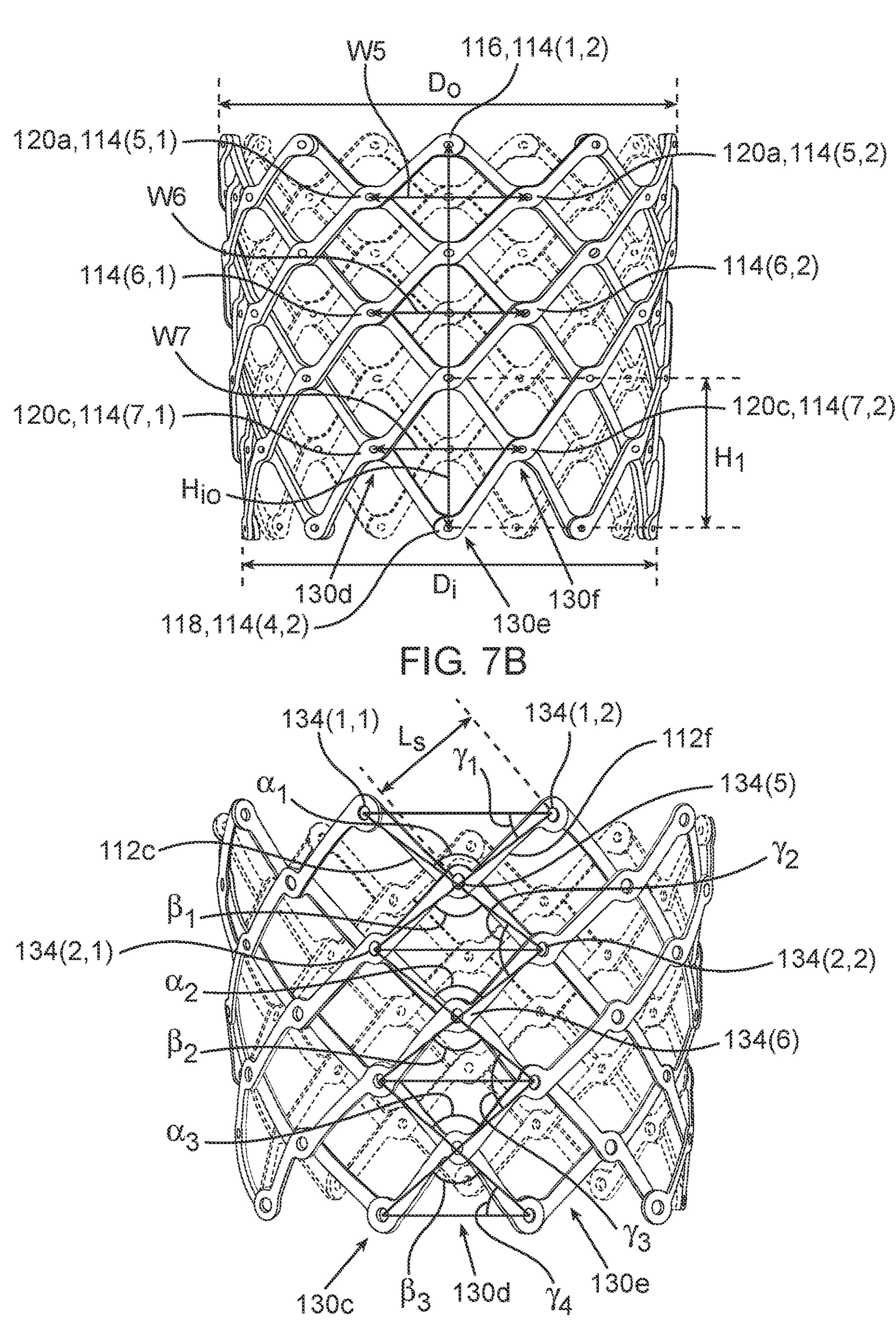

FIGS. 7A-7C illustrate views of examples of a prosthetic valve 100 (which may be expanded against an aortic annulus 14 as shown in FIG. 7A), demonstrating structural components of the prosthetic valve 100 and dimensions of the prosthetic valve 100 that can be identified and determined by the dimension determination component 220, based on analyses of images acquired by the imaging device 202 of the views shown in FIGS. 7A-7C.

The term "image", as used herein, is used for simplicity to refer to either a single acquired image or two or more acquired images.

In some examples, the techniques and systems discussed herein can evaluate images acquired during an implantation procedure of a prosthetic valve 100, and more precisely, during expansion of a prosthetic valve 100 within a desired site of implantation within a patient's body, to identify structural components of the prosthetic valve 100 such as junctions 114, strut segments 112, cells 108, cell columns 130, and outer members 140 of expansion and locking assemblies 138, and potentially structural elements of the anatomy surrounding the prosthetic valve at the site of implantation, such as the aortic walls 12, aortic annulus 14, cusps 16, and the LVOT 18. Based on identifying structural components of the prosthetic valve 100 that are visible/represented in the image, the techniques and systems can determine dimensions of the prosthetic valve 100, evaluate valve expansion diameters based on such dimensions, and provide instructions/information based thereon.

FIG. 7A shows some example dimensions that can be determined from the acquired image, including lateral distances W between junctions 114. In some examples, a process for estimating at least one expansion diameter of the prosthetic valve includes determining at least one, and optionally a plurality of, lateral distances W between junctions 114 along a non-apical cell column 130, such as lateral distances W1, W2, W3 and W4 shown in FIG. 7A.

The process can include identification of structural components required to identify a non-apical column, such as non-apical cell column **130*d* shown in FIG. 7A, bound between apical cell columns 130*c* and 130*e*. Identification of cell columns 130 can begin by identification of strut segments 112 and/or junctions 114 that may be included in such cells. Once junctions 114 are identified within an acquired image, such junctions may be classified as non-apical junctions 120 or as apical junctions such as outflow apices 116 and/or inflow apices 118**.

In some examples, identifications of the types of junctions 114 can be based solely on their positions relative to each other, and classification as apical and non-apical cell columns 130 can be based solely on junctions 114 included in each column. In some examples, the process further includes identification of strut segments 112 extending between junctions 114. Junctions 114 can be identified either by identifying apertures 134, pins 136, and/or intersections between strut segments 112. In some examples, the position of intersecting strut segments 112 can be utilized to classify the junctions 114 to non-apical junctions 120, outflow apices 116, and/or inflow apices 118.

In some examples, the process further includes identifying closed cells 108 and open cells 109, based on identified intersecting strut segments 112 and/or junctions 114 of the cells, wherein closed cells 108 will include four junctions 114 and four intersecting struts segments 112, while open cells 109 will include three junctions 114 and two strut segments 112, wherein one of the three junctions is a non-apical junctions, and the additional two junctions are outflow apices 116 or inflow apices 118.

The process can further include determinations of at least one lateral distance W along different axial positions of the non-apical cell column 130*d*, such as lateral distance W1 between junctions 114(1,1) and 114(1,2), which are outflow apices 116, lateral distance W2 between junctions 114(2,1) and 114(2,2), lateral distance W3 between junctions 114(3,1) and 114(3,2), and lateral distance W4 between junctions 114(4,1) and 114(4,2), which are inflow apices 118. The plurality of lateral distances W1-W4 are substantially parallel to each other, as shown.

The lateral distance W can be determined between two consecutive junctions at opposite lateral ends of a closed cell 108, such as lateral distances W2 and W3 shown in FIG. 7, or between two consecutive apices 116, 118, such as lateral distance W1 disposed at the outflow end 102 of the valve, or lateral distance W4 disposed at the inflow end 104 of the valve.

Dimensions such as lateral distances W (e.g., W1-W4) may be measured in pixels. In some examples, there is provided at least one constant-length structural component of the prosthetic valve 100, defined as a structural component that does not vary in length throughout the implantation procedure, and wherein the length of this component is known and can serve as a scale reference utilized to calibrate other dimensions and convert pixels to SI units, for example. In some examples, a component of the expansion and locking assembly 138, such as an outer member 140, can serve as a constant-length structural component, having a known constant outer member length Lp as shown in FIG. 7A. Other types of prosthetic valves can include other constant-length structural components, such as a commissure post attached to the frame or integrally formed therewith, having a vertical post length Lp. In some examples, a strut segment 112 can serve as a constant-length structural component, having a strut segment length Ls (see for example FIG. 7C).

Components that may serve as constant-length structural components are rigid components that do not deform and do not foreshorten or otherwise change in length during valve expansion, and that are identifiable in an acquired image, such as being radiopaque (e.g., being made of a metallic material).

It is to be understood that other components of the prosthetic valve, that need to be identified in an acquired image, can also be preferably radiopaque, such as struts 110 and segments 112 thereof, or pins 136, or should otherwise be identifiable by having borders that are radiopaque, for example apertures 134 whose borders within the metallic struts 110 can be identifiable.

Estimation of an expansion diameter of the prosthetic valve 100 can be based on at least one lateral distance W. In some examples, a single lateral distance W is determined. This may be sufficient in cases in which the prosthetic valve 100 is expanded to a cylindrical configuration, having a uniform expansion diameter along its length. In such cases, estimation of an expansion diameter at any axial position along the prosthetic valve 100, based on any lateral distance W, may be indicative of the expansion diameter along any other axial position of the prosthetic valve.

In some examples, at least two lateral distances W are determined at different axial locations along the prosthetic valve 100. A plurality of lateral distances W may be required for estimation expansion diameters at different axial positions of the prosthetic valve 100, for prosthetic valves that expand to a non-cylindrical configuration, such as the frustoconical configuration described hereinabove in conjunction with FIGS. 5A-5C. A lateral distance W measured between two junctions 114 at each axial position along the prosthetic valve 100 may be utilized for estimation of the expansion diameter at that axial position, such that two lateral distances W at different axial positions may be utilized for estimation of expansion diameter along other axial positions of the prosthetic valve 100 for example by means of mathematical interpolations or extrapolations. More than two lateral inter-junctions distance W may be determined in order to improve accuracy of the interpolation of extrapolation along other axial regions of the prosthetic valve 100.

The term "axial", as used herein, refers to a direction extending between the inflow end 104 and the outflow end 102 (which may be also referred to as a height of the valve). Reference to different axial positions refers to different heights along the prosthetic valve 100, between the inflow end 104 and the outflow end 102.

The inflow end 104 can define an inflow plane, passing through all inflow apices 118, and the outflow end 102 can similarly define an outflow plane, passing through all outflow apices 116. A plurality of lateral planes can be defined between the inflow plane and the outflow plane, parallel to each other and to the inflow and outflow planes. Any reference to a lateral plane refers to a plane between the inflow and outflow planes, that is parallel thereto.

Each lateral width W is defined along such lateral plane, wherein an expansion diameter of the prosthetic valve at the height (or axial position) of the same lateral plane can be estimated from the lateral width W. Thus, lateral width W1 can be utilized for estimation of an expansion diameter at the outflow plane, also referred to as the outflow diameter Do. Lateral width W4 can be utilized for estimation of an expansion diameter at the inflow plane, also referred to as the inflow diameter Di. Lateral width W2 can be utilized for estimation of an expansion diameter at the height of the lateral plane passing through junctions 114(2,1) and 114(2,2), and lateral width W3 can be utilized for estimation of an expansion diameter at the height of the lateral plane passing through junctions 114(3,1) and 114(3,2).

In the case of a prosthetic valve expanded to a frustoconical shape, having a non-uniform diameter, each lateral width at a different axial position can have a different magnitude. For example, W4<W3<W2<W1 as shown in FIG. 7A.

FIG. 7B shows additional example dimensions that can be determined from the acquired image, including vertical heights H and lateral distances W between junctions 114. In some examples, a process for estimating at least one expansion diameter of the prosthetic valve includes determining at least one, and optionally a plurality of, lateral distances W and/or vertical heights H between junctions 114 along an apical cell column 130, such as lateral distances W5, W6, W7 and vertical heights H1 and Hio shown in FIG. 7B.

The process can include identification of structural components required to identify an apical column, such as apical cell column 130*e* shown in FIG. 7B, bound between non-apical cell columns 130*d* and 130*f*. Identification of struts segments 112 and cell columns 130, as well as identification and classification of junctions 114, can be performed in the same manner described above with respect to identification of non-apical columns.

The process can further include determinations of at least one lateral distance W along different axial positions of the apical cell column 130*e*, such as lateral distance W5 between junctions 114(5,1) and 114(5,2), which are non-apical proximal-most junctions 120*a*, lateral distance W6 between junctions 114(6,1) and 114(6,2), and lateral distance W7 between junctions 114(7,1) and 114(7,2), which are non-apical distal-most junctions 120*c*.

The plurality of lateral distances W5-W7 are substantially parallel to each other, as shown. Lateral width W5 can be utilized for estimation of an expansion diameter at the lateral plane passing through junctions 114(5,1) and 114(5,2). Lateral width W6 can be utilized for estimation of an expansion diameter at the lateral plane passing through junctions 114(6,1) and 114(6,2). Lateral width W7 can be utilized for estimation of an expansion diameter at the lateral plane passing through junctions 114(7,1) and 114(7,2). In the case of a prosthetic valve expanded to a frustoconical shape, having a non-uniform diameter, each lateral width at a different axial position can have a different magnitude. For example, W7<W6<W5 as shown in FIG. 7B.

In some examples, lateral widths W can be determined along more than one cell column 130. For example, at least some of lateral widths W1-W4 can be determined between junctions 114 disposed at opposite lateral ends of intersecting strut segments 112 of a non-apical cell column 130*d*, and at least some of lateral widths W5-W7 can be determined between junctions 114 disposed at opposite lateral ends of intersecting strut segments 112 of a apical cell column 130*e*. Since lateral widths W1-W4 and lateral widths W5-W7 are positioned at different axial positions, such as lateral width W5 along a lateral plane positioned between the lateral planes of lateral widths W1 and W2, and lateral width W2 along a lateral plane positioned between the lateral planes of lateral widths W5 and W6, and so on, identifying lateral widths from adjacent apical and non-apical cell columns can enhance the resolution of the number of diameters estimated at different axial positions of the valve, thereby improving accuracy of interpolations or extrapolations performed to estimate an expansion diameter value at an axial position that does not cross through specific lateral junction 114 or identified lateral widths W.

According to some examples, the dimensions determined from the acquired image can include vertical heights between two junctions 114 aligned along a vertical line. For example, FIG. 7B shows an example of a height H1 between two junctions 114 of the cell that includes lateral width W7. Thus, lateral width W7 and vertical height H1 can together provide the width and height of the call through which they extend.

While H1 shows an example of a vertical height H1 extending between opposite vertical junctions of a single cell 108, other vertical heights H can be determined between opposite vertical junctions of more than one cells. For example, Hio shown in FIG. 7B spans across three cells vertically aligned with each other, and more specifically, extends between an inflow apex 118 and an outflow apex 116 vertically aligned therewith, thereby representing the vertical height of the entire frame 106 between the inflow end 104 and the outflow end 102. Other heights may span across more than one cell but less than the entire height of the frame.

In the case of a prosthetic valve expanded to a frustoconical shape, having a non-uniform diameter, cells at different axial positions along the same cell column may have different vertical heights, as shown for example in FIG. 7B, wherein H1 is longer than the vertical heights of cells vertically aligned therewith, at axial positions that are proximal thereto.

While shown in the example of FIG. 7B to be determined between junctions of an apical column, such as cell column 130*e*, it is to be understood that vertical heights can be similarly determined between junctions of a non-apical cell column, such as cell column 130*d*. In some examples, determination of dimensions from an acquired image can include at least one lateral width, at least one vertical height, and/or combinations thereof. Vertical heights may be determined for estimation of frame foreshortening during expansion thereof. Frame foreshortening can be used to derive expansion diameters based on known relation between axial foreshortening and radial expansion, and thus may serve as an additional method used for estimation of expansion diameter that can be used in combination with lateral-width based estimates, so as to improve accuracy of the estimated diameter.

In some examples, two or more vertical height H determined along two or more cell columns 130, thereby representing vertical heights H at different lateral positions across the circumference of the prosthetic valve, may be indicative of whether the valve is expanded in an even or an un-even manner along its circumference, and the extent of un-evenness at different circumferential positions during expansion thereof.

FIG. 7C shows additional example dimensions that can be determined from the acquired image, including strut opening angles α, β, γ, and lateral distances W between junctions 114 that can be derived therefrom. An opening angle can include a vertically oriented opening angle α defined at the intersection between two strut sections 112, and oriented at a vertical direction from the point of intersection. For example, FIG. 7C shows a vertically oriented opening angle α1 defined between strut sections 112*c* and 112*f*, intersecting at a junction 114 that can be identified by aperture 134(5).

A plurality of angles, such as α1, α2 and α3 can be determined, for example—being vertically aligned along the same cell column 130, such as cell column 130*d* shown in FIG. 7C. While vertically oriented opening angle α1, α2 and α3 may be oriented proximally, vertically oriented opening angle β1, β2 and β3, which are corresponding alternate angles facing the distal direction, can be determined in a similar manner.

An opening angle can similarly include a laterally oriented opening angle γ, oriented at a lateral direction from the point of intersection. In some cases, the laterally oriented opening angle γ is defined at the intersection between two strut segments 112. For example, γ2 and γ3 shown in FIG. 7C are defined between intersecting strut segments 112, and are actually consecutive and supplementary angles of α2 and α3 (or β1 and β2). Another type of a laterally oriented opening angle γ can be defined between a strut segment 112 and a lateral width W intersecting therewith. For example, γ1 can be defined between strut section 112*f* and the lateral width between apertures 134(1,1) and 134(1,2), which is actually W1 shown in FIG. 7A between the same junctions (and not annotated again in FIG. 7C to avoid clutter). Thus, any of $\gamma 1$ or $\gamma 4$ shown in FIG. 7C can be about half the size of consecutive and supplementary angles of $\alpha 1$ and $\beta 3$, respectively.

Determination of an opening angle from an acquired image, can be used in combination with a known strut section length Ls, to derive the appropriate lateral width W extending between the corresponding opposite lateral junctions 114. If the junctions 114 are identified by their apertures 134, as shown in FIG. 7C for example, a strut segment length Ls may be defined as the length between the apertures 134 at both ends of the strut segment 112. This length Ls can be slightly angled with respect to the edges of the strut segment 112 for cases in which the apertures 134 on both ends thereof are offset with respect to each other, as shown.

Thus, determination of $\alpha 1$ can be used in combination with the known length Ls to derive lateral width W1 between apertures 134(1,1) and 134(2,1). It is to be understood that any reference to dimensions determined relative to junctions 114 may be similarly applicable to the same dimensions being determined relative to apertures 134 or pins 136, at similar positions across the frame 106, if apertures 134 or pins 136 are detectable in the acquired image and are utilized to identify the spatial positions of the apertures 134.

Determination of opening angles such as angles $\alpha$, $\beta$, $\gamma$ may be advantageous since the angles may serve as non-dimensional measures utilized for estimation of various distances, such as lateral lengths W and/or vertical heights H, without measuring such distances as amount of pixels that are later calibrated to lengths in SI units, for example. Nevertheless, in some examples, both direct determination of distances such as lateral widths W and/or vertical heights H, and determination of opening angles from which some of these distances can be derived, are performed, for example to improve accuracy of the process of assessment.

Advantageously, the proposed methods do not rely on pre-measured relations between dimensions, such as opening angles or distances, and expansion diameters of the valve, and do not compare dimensions determined from the acquired images with tables or graphs storing such relations.

Figure 8:
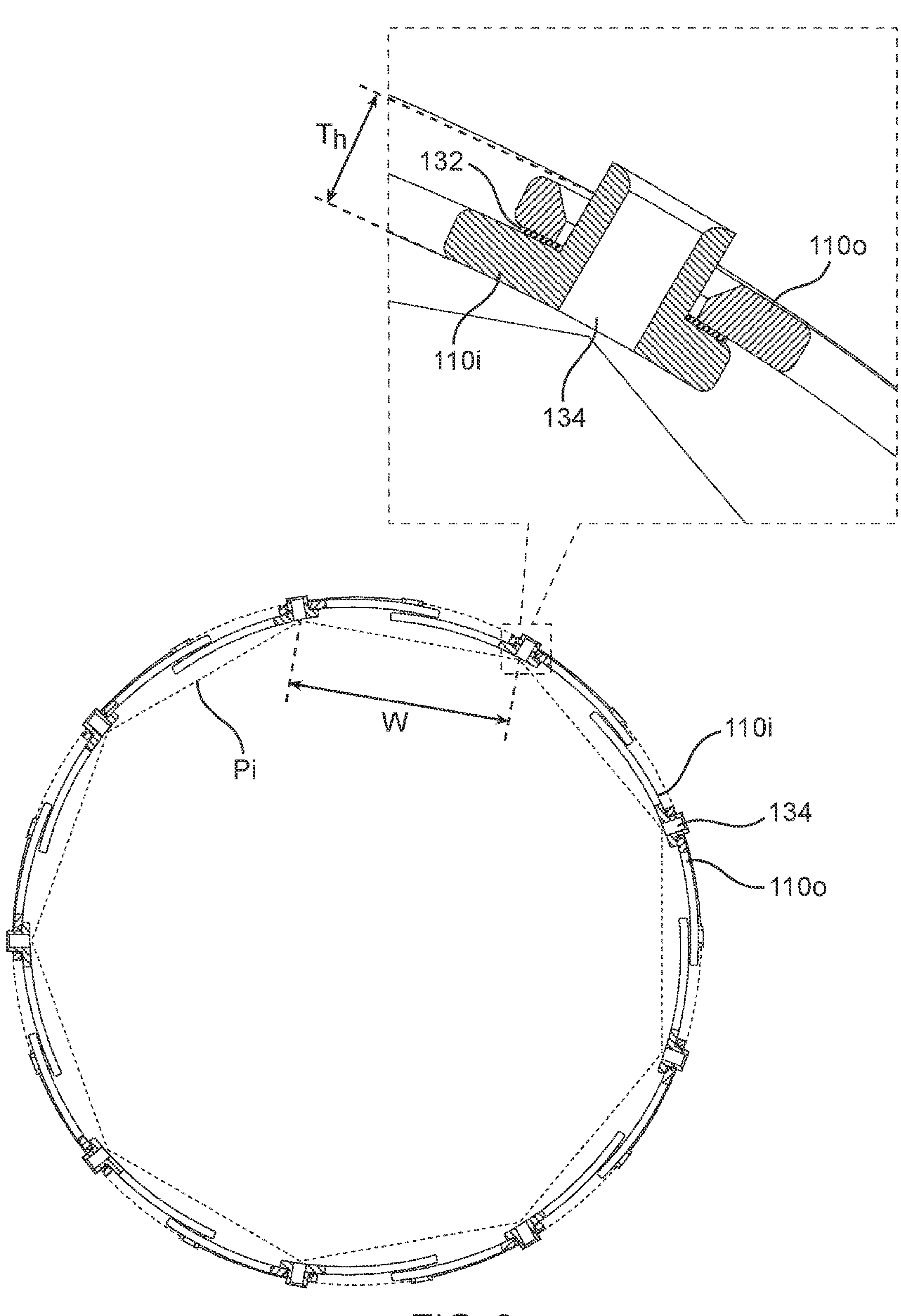
FIG. 8 shows a lateral cross-section of a prosthetic valve across a selected lateral plane between the inflow end and the outflow end, according to some examples.

FIG. 8 shows a lateral cross-section of a prosthetic valve 100 across a selected lateral plane between the inflow end and the outflow end. As mentioned above, a prosthetic valve 100 can include two layers of struts 110 intersecting with each other, including inner struts 110*i* and outer struts 110*o*, as shown. The junctions 114 can be identified the apertures 134 extending therethrough (shown in the zoomed-in region of FIG. 8), or pins 136 extending through such apertures (pins not illustrated in FIG. 8 for clarity). As further shown in FIG. 8, each aperture 134 can extend through a portion of a corresponding inner strut 110*i*, such that the lateral widths W discussed hereinabove, are actually measured between apertures 134 extending through the inner struts 110*i*.

As further shown in FIG. 8, the plurality of apertures 134 defined across the circumference of the frame 106 along a single lateral plane can define an internal polygon Pi, that includes a plurality of edges, each having a polygon edge length Le. The estimated lateral width W, determined at the level of the lateral plane shown in FIG. 8, serves as the length of each edge of the internal polygon Pi. Thus, the internal polygon Pi can be derived from the lateral width W determined at the level of the corresponding lateral plane, multiplied by the number of edges, which is equal to the number of junctions 114 disposed around the circumference of the valve at the corresponding lateral plane.

The outer diameter of the valve can be defined for a circumcircle extending over the outer surface defined by the outer struts 110*o*, illustrated as a dotted circumcircle circumscribing the outer struts 110*o* in FIG. 8. The vertices of the internal polygon Pi are internally offset from the outer circumcircle by the thickness Th of the frame at the junctions 114, between the inner surface of the inner strut 110*i* and the outer surface of the outer strut 110*o*. The thickness Th may include the thickness of the inner strut 110*i* and the thickness of the outer strut 110*o*. In some examples, the frame 106 includes a washer 132 situated between the inner strut 110*i* and the outer strut 110*o* at each junction 114, such that the thickness Th includes the thickness of the washer 132 as well. In some examples, the pin 136 or other type of fastener extending through the aperture 134 can include a head that extends radially outward beyond the outer surface of the outer strut 110*o* (not shown in FIG. 8), such that the thickness Th includes the additional portion of pin head, resulting in an overall thickness Th extending between the inner surface of inner strut 110*i* and outer surface of the head of pin 136.

Thus, the process of estimating an outer diameter of the prosthetic valve 100 can include estimating the outer diameter, at a specific axial position, as the diameter of a circumcircle approximated around an internal polygon having edges equal in length to the lateral width determined for the same plane, wherein the circumcircle may be offset from the vertices of the internal polygon by a thickness Th of the junctions. In some examples, the outer diameter can be estimated by the equation:

$$Dc = \frac{N \cdot W}{\pi} \cdot \frac{L_{actual}}{L_{pixels}} + 2 \cdot Th$$

wherein Dc is the desired estimated outer diameter of the prosthetic valve at the relevant lateral plane (i.e., at the relevant axial position), N is the number of edges of the internal polygon Pi, such that N times W is the perimeter of the internal polygon Pi. $L_{actual}$ is the length of the constant outer member length, which is a pre-measured known value that can be the outer member length (or commissural post length) Lp, or a strut section length Ls, and $L_{pixels}$ is the length measured in pixels from the acquired images, such that the ratio of $L_{actual}$ to $L_{pixels}$ serves as a calibration for the size of lateral width W that can be determined in pixels from the acquired image. The junction thickness Th, which can be at least as great as the combined thickness of the inner and outer struts 110*i* and 110*o*, respectively, compensates for the additional offset of the circumcircle from the vertices of the internal polygon Pi.

The portion of the formula without the adding twice the thickness Th may represent the diameter of a circumcircle surrounding the internal polygon Pi and extending along its vertices, which is the inner diameter of the prosthetic valve 100 at the same lateral plane. Thus, both inner and outer diameters can be estimated by the above-mentioned formula, without and with the additional of the offsetting parameter 2Th.

It is to be understood that a reference to any diameter D, unless stated otherwise, is to an outer diameter Dc.

While Dc can be estimated at discrete axial positions along which lateral widths W can be determined, based on lateral junctions 114, an outer diameter of interest may be desired at an axial position that is not in level with specific junctions 114, in which case the desired outer diameter, one or more, can be interpolated or extrapolated from two or more outer diameter estimated at axial positions for which lateral widths have been determined.

For example, FIG. 7A shows a prosthetic valve 100 expanded against an aortic annulus 14. The outer diameter of the valve at the annular level Da should not exceed a maximal value, that can be determined, for example, from pre-CT images for a specific patient, so as to reduce risk of annular rupture. In the example illustrated in FIG. 7A, the annular outer diameter Da is positioned at a level that does not coincide with specific junctions 114, shown in the illustrated example to be positioned slightly above (i.e., proximal to) the level of the non-apical distal-most junctions 120*c* (annotated, for example, in FIG. 7B). If at least one outer diameter Dc is estimated at lateral planes on both sides of the annular level, such as at the level of W3 and at the level of W4 (which may be the inflow outer diameter Di), the annular outer diameter Da can be interpolated therefrom. In at least two outer diameters Dc are estimated at lateral planes on one side of the annular level (either proximal or distal), such as the levels of W2 and W3, the annular outer diameter Da can be extrapolated therefrom.

In some examples, the techniques and systems discussed herein can use one or more algorithms to determine a distance/dimension associated with the prosthetic valve 100, such as an algorithm that converts a number of pixels or a distance between pixels in an acquired image to a distance/dimension of the prosthetic valve 100.

According to some examples, a single outer diameter Dc is estimated by the control circuitry 210 and/or the dimension determination component 220, and optionally presented to a user (e.g., a physician, a technician, a radiologist, etc.) for example via at least one I/O interface 216 (e.g., a display), and/or stored in a database 226, and/or transmitted via at least one network interface 212. A single outer diameter may be applicable, as mentioned above, for cases in which the prosthetic valve 100 is expanded to a cylindrical shape having a uniform diameter along its length, or in cases wherein the outer diameter of interest is at a single axial position, and while other outer diameters may be estimated for interpolation or extrapolation of the desired single outer diameter of interest, they may not be shown.

According to some examples, more than one outer diameter Do is estimated by the control circuitry 210 and/or the dimension determination component 220, and optionally presented to a user (e.g., a physician, a technician, a radiologist, etc.) for example via at least one I/O interface 216 (e.g., a display), and/or stored in a database 226, and/or transmitted via at least one network interface 212. For example, several outer diameters, such as the inflow diameter Di, outflow diameter Do, annular diameter Da, and potentially additional diameter at additional axial positions, may be estimated and potentially presented to the user.

A method of estimating at least one outer diameter of a prosthetic valve can include a series of steps, that may be performed during prosthetic valve expansion. The method can include a step of acquiring one or more images of the prosthetic valve during a valve expansion procedure by an imaging device 202, such as a fluoroscopy device which is conventionally utilized for imaging during prosthetic valve implantation procedures. The control circuitry 210 can receive the one or more acquired images (e.g., fluoroscopy images) from the imaging device 202. The acquired image can include components of the prosthetic valve 100 that can be radiopaque components, such as the frame 106 comprised of struts 110 and segments 112 thereof, and optionally expansion and locking assemblies 138 that can be attached to the frame 106.

The method further comprises a step of analyzing the acquired image to identify structural components of the prosthetic valve 100, which can be performed by the control circuitry 210, including by the dimension determination component 220 and/or image processing component 224 that can be embodied within control circuitry 210. Identification of structural components can include identification of basic components of the prosthetic valve 100 and identification of complex structures of the prosthetic valve 100. For example, identification of basic components can include radiopaque components, such as strut segments 112, outer members 140 of expansion and locking assemblies 138, and junctions 114. Junctions 114 can be identified as the intersection regions between struts 110, by identifying the borders of apertures 134 extending there-through, by identifying washers 132 disposed between inner and outer struts, and/or by identifying pins 136 or other fasteners extending through the junctions (e.g., through apertures 134).

Complex structures may be structures that are combined from, or include, a plurality of the basic identified components, and may include cells 108 (e.g., closed cells) that are combined from four strut segments 112 intersecting at four junctions 114, and cell columns 130 that may include several cells 108 vertically aligned with each other. An association between a complex structure such as a cell 108 or a cell column 130 and the basic components comprised therein can be also identified, for example associating each strut segment 112 with the cells 108 and/or the cell columns 130 it's comprised in, and associating each junction 114 with the strut segments 112, the cells 108 and/or the cell columns 130 it's comprised in. Each strut segment 112 can be shared by, and associated with, more than one cell 108 and more than one cell column 130. Each junction 114 is associated with more than one strut segment 112 (e.g., associated with two strut segment 112 in the case of an apex, or with four strut segments 112 in the case of a non-apical junction), and may be shared by and associated with more than one cell 108 and more than one cell column 130.

In some examples, the step of analyzing the acquired image to identify structural components further includes classifying at least some of the basic identified components and/or the complex structures. In some examples, the step of classifying includes classification of the type of each identified junction 114, for example as an outflow apex 116, an inflow apex 118, or a non-apical junction 120. In some examples, the step of classifying includes classification of the type of each cell 108 as a closed cell or an open cell 109. In some examples, the step of classifying includes classification of the type of each cell column 130 as an apical cell column or a non-apical cell column.

In some examples, the step of analyzing the acquired image to identify structural components further includes identification of the spatial position of identified components, such as basic components, and more specifically such as the spatial position of junctions 114, and further identifying junctions that are laterally aligned with each other. This step can further identify junctions that are laterally aligned with each other and belong to the same cell 108 and/or the same cell column 130.

In some examples, control circuitry 210, including dimension determination component 220 and/or image processing component 224 that may be embedded therein, can use one or more image processing techniques that can use one or more models, such as machine-trained model, user-trained model, or another model that has been trained to identify and classify features in acquired images.

In some examples, control circuitry 210 can provide a user interface to a user and/or receive input regarding one or more dimensions and/or structural components of the prosthetic valve, including positions and/or classifications thereof. For example, the control circuitry 210 can generate user interface data representing a user interface that includes an acquired image and/or send the user interface data to a display device for display of the user interface, including the acquired image. A user can view the acquired image through the interface and provide input identifying positions of structural components, such as junctions 114, strut segment 112, outer member 140) and the like. A user can further classify specific structural components, such as the type of junction 114 and/or junctions that are laterally aligned with each other.

In one example, a user can designate a first point/location on an image, that can be a first junction, and a second point/location on an image, that can be a second laterally aligned with the first junction, and request that a distance, which is a lateral width W, be calculated between the first junction and the second junction. The same can be performed for vertically aligned junctions for calculating a vertical height. Similarly, a user can designate a first strut segment (that may be, in some implementations, indicated by pointing at two points/locations through which the strut segment extends) and a second strut segment that is intersecting therewith, requesting that an opening angle be calculated between the first strut segment and the second strut segment.

The various steps described hereinabove for analyzing an acquired image can be performed in any order. For example, the order of execution can include identification of basic components of the prosthetic valve and classification thereof, wherein the step of identification of complex structures is performed after classification of at least some components, wherein the classification facilitates identification of some of the complex structures. Classification may then be performed again for the identified complex structures. In some cases, identification of the spatial position of basic components can be performed prior to classification thereof, wherein the spatial position facilitates such classification (for example, classifying a junction 114 as an outflow apex 116, and inflow apex 118, a non-apical proximal most junction 120*a*, a non-apical distal-most junction 120*c*, other non-apical junction 120 and the like).

Thus, the method further includes a step of determining at least one dimension of the prosthetic valve, performed by the control circuitry, and more specifically, by a dimension determination component that can be embedded therein or associated therewith. The at least one dimension will always include at least one lateral width W. In some examples, several (i.e., two or more) lateral widths W are determined, each between two laterally spaced junctions 114. In some examples, several lateral widths W are determined at different axial positions of the same cell column 130, that can be either an apical cell column or a non-apical cell column. In some examples, at least two lateral widths W of two different cell columns 130 are determined. For example, one or more lateral widths W can be determined for a first cell column, which can be an apical cell column, and one or more additional lateral widths can be determined for a second cell column, which can be a non-apical cell column, wherein both apical and non-apical cell columns 130 can be adjacent cell columns, that may share some of the strut segment 112 and junctions 114.

The determination of the at least one lateral width W can be performed by directly estimating a distance between two laterally aligned junctions 114, that can be positioned opposite to each other along the same cell (a closed cell 108, or an open cell 109 in the case of inflow or outflow apices), or by first determining an opening angle defined either between intersecting strut segments and facing the lateral width W, or defined between a strut segment and a lateral width, as described hereinabove.

In some examples, the step of determining at least one dimension further includes determining at least one vertical height H. In some examples, several vertical heights H are determined at different lateral positions of the prosthetic valve, in which case the method can further include a step of comparing between the different vertical heights H to evaluate whether the prosthetic valve is expanded in an even or non-even manner across its circumference, and if the expansion is non-even, provide information regarding the extent to which the expansion is non-even.

In some examples, the step of analyzing the image to identify structural components of the prosthetic valve includes identifying a constant-length structural component, and the method further includes a step of obtaining a pre-stored length of the constant-length structural component. For example, an outer member 140 of an expansion and locking assembly 138, or another type of a commissural post that is either attached to, or integrally formed with, the frame 106, can be identified as a constant-length structural component and classified or tagged as such. The length of the outer member 140 can be pre-stored, for example in the memory 218 and any component thereof (such as database 226), and this pre-stored length Lp of the outer member 140) (or other commissure post) can be retrieved (e.g., from the memory) by the control circuitry 210, and associated with the identified outer member 140.

In another example, strut segment 112 can be identified as a constant-length structural component and classified or tagged as such. While strut segments 112 pivot about junctions 114 during valve expansion, their length remain constant and may be pre-store, for example in the memory 218 and any component thereof (such as database 226), and this pre-stored length Ls of the strut segment 112 can be retrieved (e.g., from the memory) by the control circuitry 210, and associated with the identified strut segment 112 serving as the constant-length structural component.

The method further includes a step of estimating at least one outer diameter of the prosthetic valve, performed by the control circuitry, based on the at least one lateral width W determined at the level (i.e., at the axial position) of the estimated outer diameter, and the retrieved length associated with the identified constant-length structural component. This estimation can follow the above-mentioned formula described in conjunction with FIG. 8 hereinabove, which is based on calculation of a diameter of a circumcircle surrounding an approximated internal polygon Pi comprising a known number of edges N, each having a length equal to the determined lateral width W. The number of edges N is constant and is known for a specific prosthetic valve type, and is equal to the number of junctions 114 surrounding the frame 106 across the corresponding lateral plane. FIG. 8 shows a specific example of an internal polygon Pi having nine edges extending between nine junctions 114. The retrieved length associated with the constant-length structural component serve to convert distances from pixels to length units.

In some examples, the step of estimating at least one outer diameter further is further includes adding a product of the thickness Th of a junction 114 (as shown in the formula hereinabove, the product can be doubling the thickness Th), compensating for the additional radial offset of the circumcircle from the vertices of the internal polygon Pi.

In some examples, the step of estimating at least one outer diameter includes estimated a plurality of outer diameters, each at a different axial position along the length of the prosthetic valve, and each based on a lateral width W determined at the axial position of the corresponding estimated outer diameter.

In some examples, the step of estimating at least one outer diameter further includes estimating at least one outer diameter at an axial position for which a lateral width has not been determined, by extrapolating or interpolating from at least two outer diameters estimated from lateral widths W determined at the axial positions thereof. In some examples, at least one outer diameter is extrapolated from at least two outer diameters estimated from lateral widths W determined at axial positions on one side thereof, such as proximal or distal thereto. In some examples, at least one outer diameter is interpolated from at least two outer diameters estimated from lateral widths W determined at axial positions on both sides thereof, i.e., both proximal and distal thereto.

In some examples, the at least one outer diameter includes the inflow diameter Di and/or the outflow diameter Do. In some examples, the at least one outer diameter includes the annular diameter Do.

Any of the steps of identifying a constant-length structural component and retrieving a pre-stored length of the constant-length structural component and associating the length with the identified constant-length structural component, can be performed at any stage prior to the step of estimating at least one outer diameter.

The above-mentioned steps can be repeated for several stages of valve expansion, so as to monitor the outer diameter of the valve at a desired axial position (one or more), such as the annular diameter, inflow/outflow diameters, and potentially additional diameter in-between.

In some examples, at least one diameter threshold can be pre-stored for at least one axial position of the prosthetic valve, for example in memory 218 or components thereof (e.g., database 226), or may be manually input by the user via the user interface provided by the control circuitry 210. The threshold may be the maximal allowable expansion diameter at the level of the native annulus (e.g., the aortic annulus 14), and may be patient specific. In some examples, such thresholds can be derived from images acquired by imaging devices, which are not necessarily the imaging device 202 described for the method hereinabove, prior to valve implantation. This may include, for example, pre-CT performed prior to prosthetic valve implantation, from which the thresholds can be derived.

According to some examples, the at least one image acquired by the imaging device 202 includes tissues of the anatomical region at the region of implantation, from which the aortic annulus 14 can be identified in a similar manner to that described for identification of structural elements of the prosthetic valve 100 hereinabove. In some examples, the method includes a step of identifying the borders of the native annulus 14 against which the prosthetic valve is to be expanded, and determining a distance between opposite walls of the annulus 14, indicative of the diameter of the native annulus 14, from which the threshold for the annular diameter Da of the prosthetic valve can be determined.

According to some examples, an estimated outer diameter is compared with a threshold retrieved (for example, by the control circuitry from the memory) for the corresponding axial position (e.g., the level of the annulus), and a warning may be generated if the estimated outer diameter exceeds the threshold.

Throughout the entire process, the control circuitry 210 can generate graphic interface data that can be relayed to a display device. The graphic interface data can include the acquired images, and/or any of the identified structural components, determined dimensions and/or estimated outer diameters, that can be either tagged or otherwise graphically layered over the acquired image, or presented separately therefrom, in any form including textual and/or graphical representations thereof.

An advantage conferred by the systems and the methods disclosed herein, is that they enable continuous real-time diameter monitoring during prosthetic valve expansion, thereby providing valuable feedback to the clinician with respect to the valve expansion within the native anatomy. This valuable information may assist in preventing, or at least reducing, potential trauma to a tissue (e.g., the annulus). The clinician can continuously readjust the diameter of the prosthetic valve 100 as necessary, until the prosthetic valve 100 is expanded to a diameter that best fits the native annulus. For example, a diameter which is sufficient to anchor the prosthetic valve 100 in place against the surrounding tissue, with little or no paravalvular leakage, and without over-expanding the prosthetic valve 100 so as to avoid, or reduce the risk of, native annulus rupture.

Figure 9A:
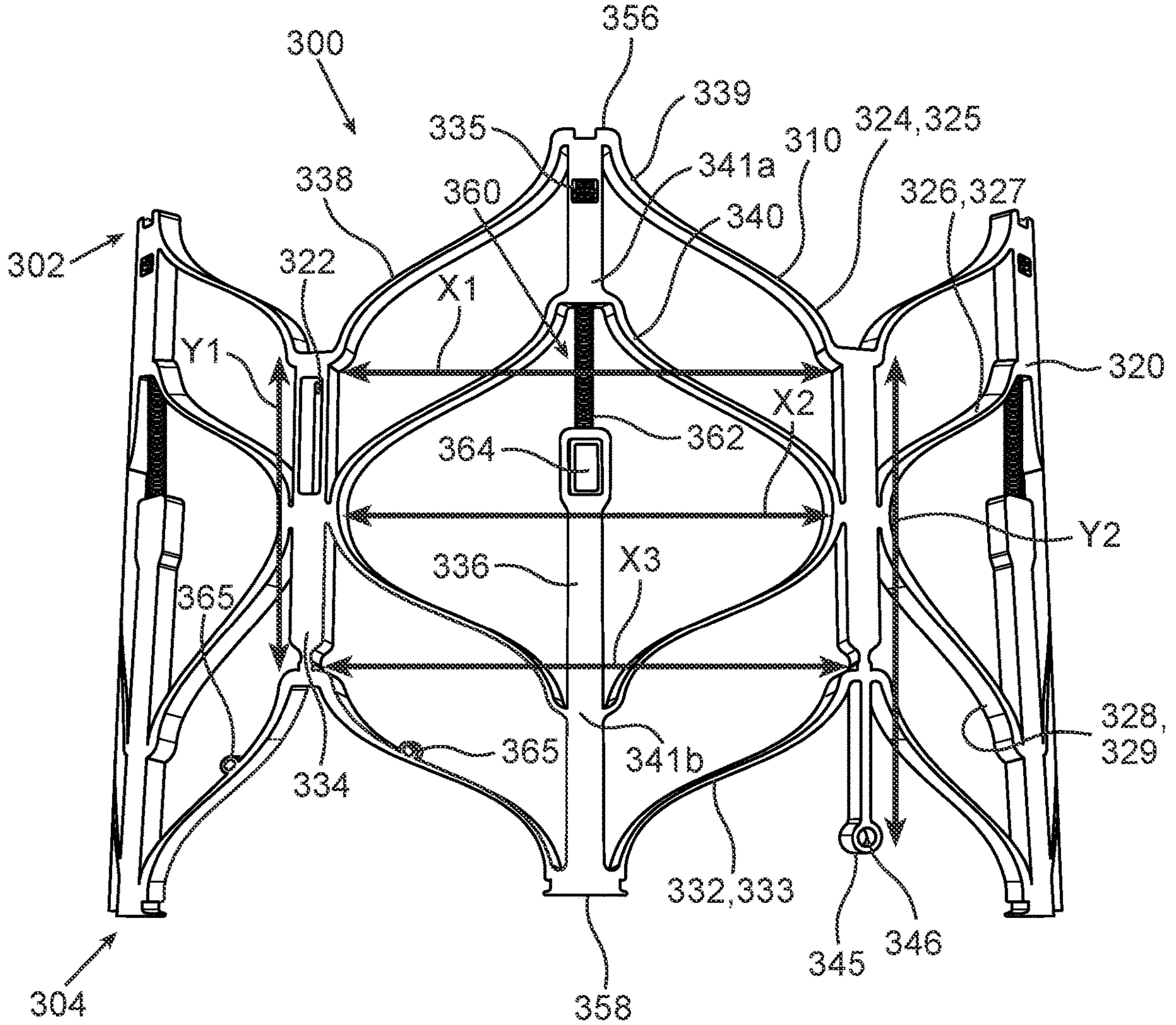
FIGS. 9A-9B show structural components and dimensions of another type of a prosthetic valve that can be identified and determined from acquired images, according to some examples.
Figures 9B, 9C:
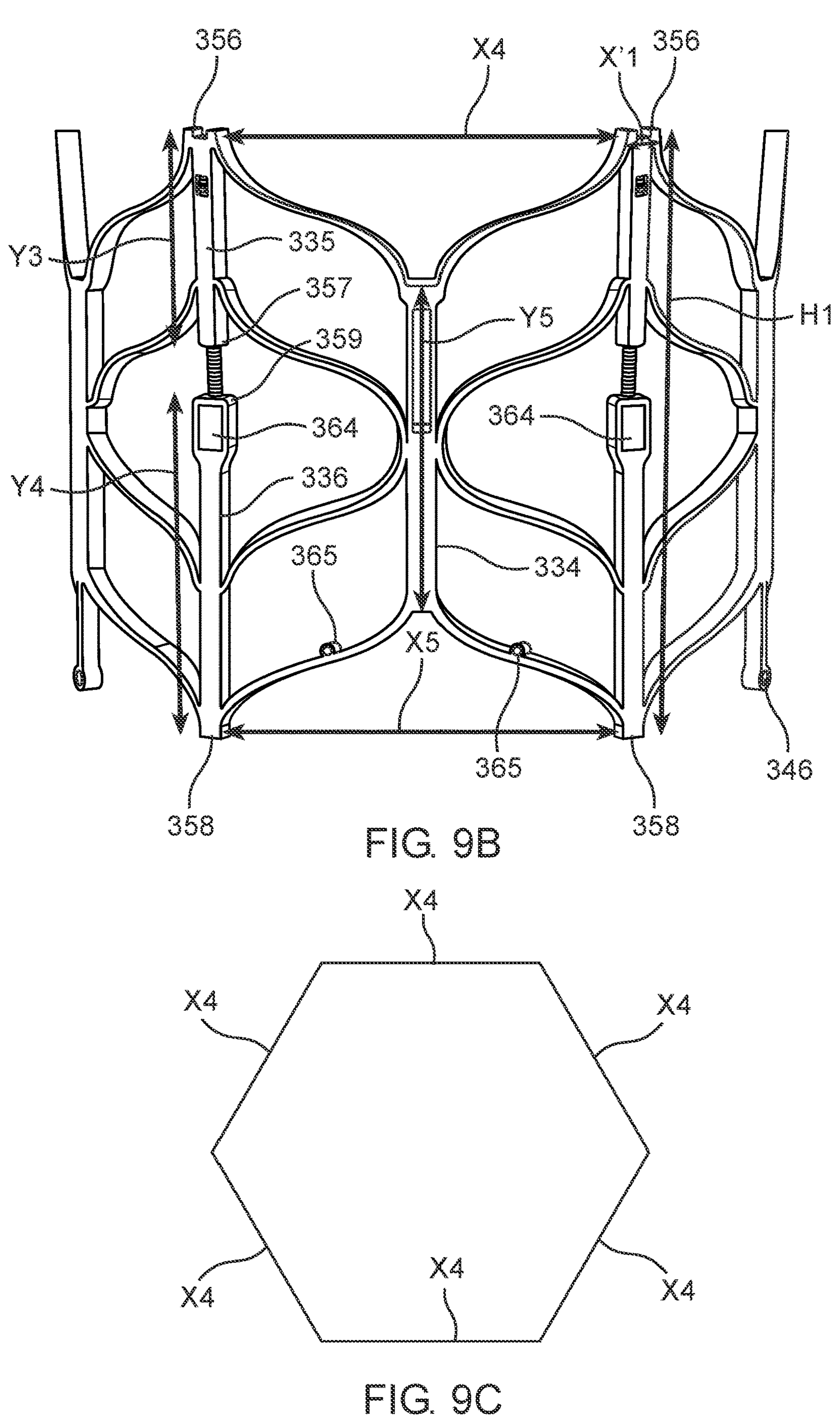
FIG. 9C shows a schematic representation of a polygon shape of the prosthetic valve across a lateral plane, according to some examples.

Reference is now made to FIGS. 9A-9C, describing measurements of a different type of prosthetic valve. Particularly, FIG. 9A shows a first partial view of another example of a mechanically expandable prosthetic valve 300 and FIG. 9B shows a second partial view of prosthetic valve 300, without soft components (such a skirt and a leaflet assembly). Similar to prosthetic valve 100, prosthetic valve 300 includes an annular frame 310 which can be a unitary lattice frame made of a set 320 of intersecting struts, defined between an outflow end 302 and an inflow end 304. As shown above in relation to prosthetic valve 100, a leaflet assembly (not shown), as well as an inner skirt and/or an outer skirt can be provided, however in the interest of brevity these components are not described.

Unlike prosthetic valve 100, which is representative of a mechanically valve that includes two layers of struts hinged to each other at their intersecting junctions, the prosthetic valve 300 is representative of another valve type that can be expanded utilizing a mechanical mechanism, having a unitary frame with a single layer of struts, as will be described in greater detail hereinbelow. In some examples, the prosthetic valve 300 can be radially expanded by maintaining the inflow end 304 at a fixed position while applying a force in the axial direction against the outflow end 302 toward the inflow end 304. Alternatively, the prosthetic valve 300 can be expanded by applying an axial force against the inflow end 304 while maintaining the outflow end 302 at a fixed position, or by applying opposing axial forces to the inflow and outflow ends 304, 302, respectively. According to some examples, a delivery apparatus (not shown) is provided which can include a plurality of actuation assemblies, configured to radially expand and/or radially compress the prosthetic valve 300 when actuated.

As shown in FIGS. 9A-B, the prosthetic valve 300 can include one or more actuators 360 mounted to and equally spaced around the inner surface of the frame 310. Each of the actuators 360 can be configured to form a releasable connection with a respective actuation assembly of a delivery apparatus (not shown).

The set 320 of interconnected struts of frame 310 of the prosthetic valve 300 illustrated in FIGS. 9A-B comprises rungs of curved struts 325, 327, 329, 333, and axial struts or posts 334, 335, 336. The curved struts define a plurality of cells 338 extending circumferentially around the frame 310. While only one side of the frame 310 is illustrated in FIGS. 9A-B, it should be appreciated that the frame 310 forms an annular structure having an opposite side that is substantially identical to the portion shown. In the illustrated embodiment, the frame 310 comprises an outflow rung 324 of curved struts 325 defining the outflow end 302: a first intermediate rung 326 of curved struts 327: an intermediate rung 328 of curved struts 329; and an inflow rung 332 of curved struts 333 defining the inflow end 304.

The cells 338 can include first cells 339 and second cells 340. Each first cell 339 can have an axially-extending elliptical shape including outflow apex 356 and inflow apex 358 disposed at the major vertices of the ellipse. Each first cell 339 can further comprise a respective second cell 340 disposed within the outer perimeter of the first cell 339. The second cell 340) can have a circumferentially-extending elliptical shape including a proximal junction 341*a* and a distal junction 341*b* disposed at the minor vertices of the ellipse. Each proximal post 335 can extend between a respective outflow apex 356 and a respective distal end 357. Each distal post 336 can extend between a respective inflow apex 358 and a respective proximal end 359. While illustrated as elliptical, it is to be understood that any of the cells 338 can have any of various other shapes, for example, hexagonal, triangular, tear drop shaped, rectangular, square, square-oval, etc.

As mentioned, the frame 310 can comprise a plurality of axially-extending struts or posts, including a plurality of proximal posts 335 and distal posts 336. The proximal posts 335 (shown as the upper posts in the illustrated example) can extend to the outflow end 302, and the distal posts 336 (shown as the lower posts in the illustrated example) can extend to the inflow end 304. Each proximal post 335 can be axially aligned with a corresponding distal post 336 for a pair of proximal and distal posts. One or more pairs of proximal and distal posts 335, 336 can be configured as actuators 360. The frame 310 can further comprise additional axial support posts 334 disposed between each pair of adjacent circumferentially disposed first cells 339, and the actuators 360 can be disposed such that they extend through and are coupled to the apices 356, 358 and junctions 341*a*, 341*b* through the first and second cells. The axial support posts 334 can be coupled together via curved struts 325, 327, 329, 333.

Each first cell 339 is formed by two curved struts 325 of the valve frame outflow rung 324 and two curved struts 333 of the valve frame inflow rung 332. Each curved strut 325 is coupled on one end to a proximal post 335 of an actuator 360 and on the other end to an axial support post 334. Each curved strut 333 is coupled on one end to a distal post 336 of an actuator 360 and on the other end to an axial support post 334.

Each second cell 340 is formed by two curved struts 327 of the valve frame first intermediate rung 326 and two curved struts 329 of the valve frame second intermediate rung 328. The lower/distal ends of the curved struts 327 and the upper/proximal ends of the curved struts 329 can be connected to the axial support posts 334. The upper/proximal ends of the curved struts 327 can be connected to a proximal post 335 of a respective actuator 360. The lower/distal ends of the curved struts 329 can be connected to a distal post 336 of the respective actuator 360.

Each proximal post 335 can extend through and be coupled to outflow apex 356 and proximal junction 341*a* of a respective first and second cell pair. Each distal post 336 can extend through and be coupled to inflow apex 358 and distal junction 341*b* of the respective first and second cell pair. In the illustrated embodiment, the frame 310 comprises six first cells 339 extending circumferentially in a row, with a second cell 340 within each first cell 339, and six pairs of proximal and distal posts 335, 336 coupled to a respective pair of cells 339, 340. However, in other embodiments, the frame 310 can comprise a greater or fewer number of first cells 339 within a row, and a correspondingly greater or fewer number of second cells 340) and/or pairs of posts 335, 336.

In some embodiments, each pair of posts 335, 336 can be configured as an actuator 360. For example, in the illustrated embodiment, each of the six pairs of posts 335, 336 is configured as an actuator 360. In other embodiments, not all pairs of posts 335, 336 need be actuators. Where a pair of posts 335, 336 is configured as an actuator, a threaded rod 362 extends through each post of 339, 340 of the pair to effect radial compression and expansion of the frame 310. The distal post 336 can comprise a threaded nut 364 disposed at a proximal end portion thereof and configured to engage the threaded rod 362. Rotation of the threaded rod 362 in a first direction (e.g., clockwise) can cause corresponding axial movement of the proximal and distal posts 335, 336 toward one another, expanding the frame 310, and rotation of the threaded rod 362 in a second direction (e.g., counterclockwise) causes corresponding axial movement of the proximal and distal posts 335, 336 away from one another, compressing the frame. As the frame 310 moves from a compressed state to an expanded state, the gap between the proximal and distal posts 335, 336 can narrow.

Because the threaded rod 362 is secured to the frame 310 at axially spaced locations (e.g., the outflow end 302 and the inflow end 304) rotating the threaded rod 362 causes axial movement of the outflow end 302 and inflow end 304 relative to one another to cause radial expansion or compression of the frame 310. For example, moving the outflow and inflow ends 302, 304 toward one another causes the frame 310 to foreshorten axially and expand radially.

As shown in FIGS. 9A-B, the axial support posts 334 can extend longitudinally and can include commissure support member, such as commissure windows 322, at a respective portion thereof. Although commissure window 322 is illustrated as being in a proximal portion of axial support post 334, this is not meant to be limiting in any way, and in other examples, commissure window 322 can be located at a different portion of the respective axial support post 334. According to some examples, one or more of the axial support posts 334 can extend towards inflow end 304 via an extension member 345. In some examples, each extension member 345 culminates in an eyelet 346. The term "eyelet", as used herein, means a small structure exhibiting a hole. In one illustrated example, each eyelet 346 is generally circular, however this is not meant to be limiting in any way, and each eyelet 346 can exhibit any shape.

Frame 310 can further have one or more pairs of eyelets 365. In one illustrated example, eyelets 365 are generally circular, however this is not meant to be limiting in any way, and each eyelet 346 can exhibit any shape. In some examples, eyelets 365 can be utilized to secure an outer skirt (not shown). In some examples, eyelets 365 are each positioned on a respective valve frame inflow rung 332. In some examples, six eyelets 365 are provided, however this is not meant to be limiting in any way. In some examples, a pair of eyelets 365 are associated with each commissure window 322, such that each pair of eyelets 365 are positioned on opposing sides a respective commissure window 322. Although FIGS. 9A-B show eyelets 365 on valve frame inflow rungs 332, this is not meant to be limiting in any way, and eyelets can be provided on valve frame outflow rung 324, in addition to, or instead of, the eyelets 365 on valve frame inflow rungs 332.

As mentioned, FIGS. 9A-B show only one side of the frame 310. Though only one axial support post 334 comprising a commissure window 322 is shown in FIGS. 9A-B, it should be noted that the frame 310 can comprise any number of axial support posts 334, any number of which can include commissure windows 322. For example, a frame 310 can comprise six axial support posts 334, three of which also include commissure windows 322. In some embodiments, for example, a valve frame can comprise one, two, three, or four commissure windows.

When the prosthetic valve 300 is implanted at a selected implantation site within a patient, the patient's native anatomy (e.g., the native aortic annulus) may exert radial forces against the prosthetic valve 300 that would tend to compress the frame 310. However, the engagement of the threaded rod 362 with the threaded nut 364 prevents such forces from compressing the frame 310, thereby ensuring that the frame remains locked in the desired radially expanded state.

Architecture 200 is configured to estimate diameters of prosthetic valve 300 during valve expansion procedures, as described above for prosthetic valve 100. Similar to prosthetic valve 100, an image of prosthetic valve 300 is acquired by imaging device 202 and analyzed by control circuitry 210 to determine at least one lateral width, such as lateral widths X1, X2, X3, X4 or X5. In some examples, as shown in FIG. 9A, one or more lateral widths X1 are measured between proximal portions of adjacent axial support posts 334. In some examples, as shown in FIG. 9A, one or more lateral widths X3 are measured between distal portions of one or more adjacent pairs of axial support posts 334. In some examples, as shown in FIG. 9A, one or more lateral widths X2 are measured across the width of one or more cells 340. In some examples, as shown in FIG. 9B, one or more lateral widths X4 are measured between adjacent outflow apices 356. In some examples, as shown in FIG. 9B, one or more lateral widths X5 are measured between adjacent inflow apices 358.

Lateral widths are not limited to widths X1-X5 and other lateral widths can be measured. In some examples, the distance between adjacent nuts 364 is measured as a respective lateral width. In some examples, nuts 364 are provided with a higher opacity than that of the respective proximal post 335, thereby allowing control circuitry 210 to identify the nuts 364 and measure the distances therebetween. One or more vertical heights can be similarly measured, such as vertical height H1, shown in FIG. 9B, extending between an outflow apex 356 and an inflow apex 358.

Control circuitry 210 further analyses the image to identify one or more constant-length structural components. In some examples, as shown in FIG. 9A, a support post 334 can be identified as a constant-length structural component, having a length Y1 that can be measured between opposing ends of a respective axial support post 334 in the acquired image, and compared to a pre-stored value. In some examples, as shown in FIG. 9A, a support post 334 that includes an extension member 345 can be identified as a constant-length structural component having a length Y2 that can be measured between a proximal end of the respective axial support post 334 and a distal end of the respective extension member 345 extending therefrom in the acquired image, and compared to pre-stored values.

In some examples, as shown in FIG. 9B, a proximal post 335 can be identified as a constant-length structural component, having a length Y3 that can be measured between an outflow apex 356 and a respective distal end 357*a* in the acquired image, and compared to a pre-stored value. In some examples, as shown in FIG. 9B, a distal post 336 can be identified as a constant-length structural component, having a length Y4 that can be measured between an inflow apex 358 and a respective proximal end 359 in the acquired image, and compared to a pre-stored value.

Control circuitry 210 estimates at least one outer diameter of prosthetic valve 300, based at least in part on: the at least one lateral width determined at the axial position of the estimated outer diameter; and the length of the constant-length structural component. As described above in relation to prosthetic valve 100, the outer diameter can be estimated at a plurality of axial positions since prosthetic valve 300 may not present a uniform shape when open, either inside or outside the body lumen.

In some examples, as shown in FIG. 9C, the plurality of determined lateral widths form a polygon. In some examples, where frame 310 exhibits 6 sides, the plurality of determined lateral widths form a hexagon. Although FIG. 9C illustrates a hexagon formed by lateral widths X4, a similar hexagon can be formed by lateral widths X5, or other lateral widths measured at different axial positions. Using the polygon, the diameter of a circle encompassing the polygon can be determined and used for estimating the open diameter of frame 310. As described above, the circle diameter can be determined at a plurality of axial positions to estimate the diameter of frame 310 at the plurality of axial positions. Thus, deformities in frame 310 can be detected.

It is noted that defining a circle encompassing a polygon is not necessary for determining these parameters and defining an axial profile of frame 310. In some examples, a plurality of lateral widths (X1, X2, X3, X4, X5 and/or other widths) are measured and compared to each other. Differences between the measured widths can define the axial profile of frame 310.

As described above in relation to prosthetic valve 100, lateral widths can be measured in pixels and the lengths of the constant-length structural components can be used as a reference for provided a more accurate estimate of the diameter of frame 310. In some examples, as described above, the one or more constant-length structural components comprise one or more support posts 334. In some examples, the one or more constant-length structural components is the combination of a proximal post 335 and distal post 336.

In one example, the diameter D of frame 310 is calculated using the following formula:

$$\sin^{-1}\frac{X'}{D} + \sin^{-1}\frac{X}{D} - \frac{\pi}{6} = 0$$

where X is the measured axial length and X' is the width of the struts. Particularly, in some examples, the axial length X is measured between struts, so the width of the strut is taken into account when estimating diameter D.

As described above, in some examples eyelets 365 are provided. In such examples, eyelets 365 can be identified by control circuitry 210 and the position of commissure windows 322 can be determined based on the position of eyelets 365. Thus, prosthetic valve 300 can be rotated such that commissure windows 322 are positioned in a desired orientation, such as a predetermined orientation relative to the native commissures of the heart. Similarly, in some examples, the eyelets 346 of extension members 345 can be identified by control circuitry 210 and used to adjust the axial position of prosthetic valve 300, such as positioning the leaflets of prosthetic valve 300 (not shown) in a predetermined position relative to the annulus or relative to the position of a previously implanted valve. In one example, positional identification can be performed based on both eyelets 346 and eyelets 365.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A method of estimating at least one outer diameter of a prosthetic valve, comprising: acquiring, by an imaging device, an image of the prosthetic valve: analyzing, by a control circuitry, the image to determine at least one lateral width: analyzing, by the control circuitry, the image to identify a constant-length structural component: retrieving, by the control circuitry, a length of the constant-length structural component and associate the length with the identified constant-length structural component: estimating at least one outer diameter of the prosthetic valve, based at least in part on the at least one lateral width determined at the axial position of the estimated outer diameter, and the length of the constant-length structural component; and outputting an indication of the estimated at least one outer diameter.

Example 2. The method of any example herein, particularly example 1, wherein the imaging device is a fluoroscopy device.

Example 3. The method of any example herein, particularly example 1 or 2, wherein the control circuitry is communicatively coupled to a memory, wherein the memory stores executable instructions that, when executed by the control circuitry, cause the control circuitry to perform steps of the method.

Example 4. The method of any example herein, particularly any one of examples 1 to 3, wherein the step of analyzing the image to determine at least one lateral width further comprises identifying structural components of the prosthetic valve, prior to determining at least one lateral width.

Example 5. The method of any example herein, particularly example 2, wherein the step of identifying structural components comprises identifying strut segments of the prosthetic valve.

Example 6. The method of any example herein, particularly example 2 or 3, wherein the step of identifying structural components comprises identifying junctions of the prosthetic valve.

Example 7. The method of any example herein, particularly example 4, wherein identifying junctions comprises identification of boundaries of apertures extending through the junctions.

Example 8. The method of any example herein, particularly example 4, wherein identifying junctions comprises identification of pins extending through the junctions.

Example 9. The method of any example herein, particularly any one of examples 4 to 8, wherein the step of identifying structural components further comprises classifying identified junctions as at least one of: inflow junctions, outflow junctions, or non-apical junctions.

Example 10. The method of any example herein, particularly any one of examples 2 to 9, wherein the step of identifying structural components further comprises identifying of spatial positions of the identified structural components.

Example 11. The method of any example herein, particularly any one of examples 4 to 10, wherein the at least one lateral width extends between two laterally aligned junctions.

Example 12. The method of any example herein, particularly any one of examples 2 to 11, wherein the step of identifying structural components comprises identification of at least one cell.

Example 13. The method of any example herein, particularly example 5, wherein the step of identifying structural components further comprises classifying the identified cell as a closed cell or an open cell.

Example 14. The method of any example herein, particularly example 5 or 13, wherein the at least one lateral width extends between two laterally aligned junctions of the same cell.

Example 15. The method of any example herein, particularly any one of examples 2 to 5, wherein the step of identifying structural components comprises identification of at least one cell column.

Example 16. The method of any example herein, particularly example 15, wherein the step of identifying structural components further comprises classifying the identified cell column as an apical cell column or a non-apical cell column.

Example 17. The method of any example herein, particularly example 5 or 15, wherein the at least one lateral width comprises a plurality of lateral widths, each positioned at a different axial position along the length of the prosthetic valve.

Example 18. The method of any example herein, particularly example 10, wherein at least two of the plurality of lateral widths are extending between lateral junctions associated with the same cell column.

Example 19. The method of any example herein, particularly example 10 or 18, wherein the at least one identified cell column comprises at least two cell columns, and wherein the plurality of lateral widths comprises at least one lateral width extending between lateral junctions of each of the two cell columns.

Example 20. The method of any example herein, particularly any one of examples 3 to 6, wherein the step of analyzing the image to determine at least one lateral width further comprises determining at least one opening angle, and wherein the lateral width is calculated from the opening angle and a length of a strut segment.

Example 21. The method of any example herein, particularly example 7, wherein the opening angle is defined between two intersecting strut segments, and wherein the opening angle is facing the lateral width.

Example 22. The method of any example herein, particularly example 7, wherein the opening angle is defined between a strut segment and the lateral width.

Example 23. The method of any example herein, particularly example 4, wherein the prosthetic valve comprises a plurality of threaded rods and plurality of nuts, each nut screwed on to a respective threaded rod, and wherein the step of identifying structural components comprises identifying the plurality of nuts of the prosthetic valve.

Example 24. The method of any example herein, particularly example 23, wherein the at least one lateral width extends between a respective pair of the identified nuts of the prosthetic valve.

Example 25. The method of any example herein, particularly any one of examples 1 to 24, further comprising a step of analyzing, by a control circuitry, the image to determine at least one vertical height.

Example 26. The method of any example herein, particularly example 25, wherein the at least one vertical height comprises a plurality of vertical heights, and wherein the method further comprises a step of comparing between the vertical heights and generating data indicative of whether the expansion of the prosthetic valve is non-even.

Example 27. The method of any example herein, particularly any one of examples 1 to 6, wherein the constant-length structural component is an outer member of an expansion and locking assembly coupled to a frame of the prosthetic valve.

Example 28. The method of any example herein, particularly any one of examples 1 to 26, wherein the constant-length structural component is a strut segment of the prosthetic valve.

Example 29. The method of any example herein, particularly any one of examples 1 to 28, wherein the step of estimating at least one outer diameter comprises calculating a diameter of a circumcircle surrounding an internal polygon defined between junctions disposed around the prosthetic valve at a corresponding lateral plane, wherein the length of each of the edges of the internal polygon is the lateral width determined at the axial position of the lateral plane, and wherein the calculation further includes conversion of distances from pixels to length units based at least in part on the length of the constant-length structural component.

Example 30. The method of any example herein, particularly example 14, wherein the calculation further includes adding a product of thickness of a junction.

Example 31. The method of any example herein, particularly example 30, further comprising a step of estimating at least one inner diameter by executing the same calculation but without adding a product of the thickness of a junction thereto.

Example 32. The method of any example herein, particularly any one of examples 31 to, wherein the step of estimating at least one outer diameter comprises estimating at least two outer diameters, each based on a lateral width determined at a different axial position.

Example 33. The method of any example herein, particularly example 32, wherein the step of estimating at least one outer diameter further comprises estimating at least one outer diameter at an axial position for which a lateral width has not been determined.

Example 34. The method of any example herein, particularly example 33, wherein the outer diameter at an axial position for which a lateral width has not been determined, is extrapolated from at least two outer diameters estimated from lateral widths determined at axial positions on one side thereof.

Example 35. The method of any example herein, particularly example 33, wherein the outer diameter at an axial position for which a lateral width has not been determined, is interpolated from at least two outer diameters estimated from lateral widths determined at axial positions on both sides thereof.

Example 36. The method of any example herein, particularly any one of examples 1 to 35, wherein the at least one estimated outer diameter is selected from: the inflow diameter, the outflow diameter, and/or the annular diameter.

Example 37. The method of any example herein, particularly any one of examples 1 to 36, further comprising: identifying, by the control circuitry, a one or more markers; responsive to the identified one or more markers, identifying, by the control circuitry, one or more commissures of the prosthetic valve; and outputting an indication of a position of the identified one or more commissures.

Example 38. The method of any example herein, particularly example 37, wherein the one or more markers comprises a plurality of eyelets, each pair of eyelets positioned on opposing sides of a respective commissure.

Example 39. The method of any example herein, particularly any one of examples 1 to 36, further comprising: identifying, by the control circuitry, one or more markers; responsive to the identified one or more markers, identifying, by the control circuitry, the position of the prosthetic valve; and outputting an indication of the position of the prosthetic valve.

Example 40. The method of any example herein, particularly example 39, wherein the one or more markers comprise one or more eyelets, each of the one or more eyelets positioned on a respective extension member extending from the prosthetic valve.

Example 41. A computing system comprising: a control circuitry; and a memory communicatively coupled to the control circuitry and storing executable instructions that, when executed by the control circuitry, cause the control circuitry to perform operations comprising: receiving an image, acquired by an imagine device, of a prosthetic valve: analyzing the image to determine at least one lateral width: analyzing the image to identify a constant-length structural component: retrieving a length of the constant-length structural component and associate the length with the identified constant-length structural component: estimating at least one outer diameter of the prosthetic valve, based at least in part on the at least one lateral width determined at the axial position of the estimated outer diameter, and the length of the constant-length structural component; and outputting an indication of the estimated at least one outer diameter.

Example 42. The computing system of any example herein, particularly example 41, wherein the image is a fluoroscopy image.

Example 43. The computing system of any example herein, particularly example 41 or 42, wherein analyzing the image to determine at least one lateral width further comprises identifying structural components of the prosthetic valve, prior to determining at least one lateral width.

Example 44. The computing system of any example herein, particularly example 43, wherein identifying structural components comprises identifying strut segments of the prosthetic valve.

Example 45. The computing system of any example herein, particularly example 43 or 44, wherein identifying structural components comprises identifying junctions of the prosthetic valve.

Example 46. The computing system of any example herein, particularly example 45, wherein identifying junctions comprises identification of boundaries of apertures extending through the junctions.

Example 47. The computing system of any example herein, particularly example 45, wherein identifying junctions comprises identification of pins extending through the junctions.

Example 48. The computing system of any example herein, particularly any one of examples 45 to 47, wherein identifying structural components further comprises classifying identified junctions as at least one of: inflow junctions, outflow junctions, or non-apical junctions.

Example 49. The computing system of any example herein, particularly any one of examples 43 to 48, wherein identifying structural components further comprises identifying of spatial positions of the identified structural components.

Example 50. The computing system of any example herein, particularly any one of examples 45 to 49, wherein the at least one lateral width extends between two laterally aligned junctions.

Example 51. The computing system of any example herein, particularly any one of examples 43 to 50, wherein identifying structural components comprises identification of at least one cell.

Example 52. The computing system of any example herein, particularly example 51, wherein identifying structural components further comprises classifying the identified cell as a closed cell or an open cell.

Example 53. The computing system of any example herein, particularly example 19 or 52, wherein the at least one lateral width extends between two laterally aligned junctions of the same cell.

Example 54. The computing system of any example herein, particularly any one of examples 43 to 53, wherein identifying structural components comprises identification of at least one cell column.

Example 55. The computing system of any example herein, particularly example 54, wherein identifying structural components further comprises classifying the identified cell column as an apical cell column or a non-apical cell column.

Example 56. The computing system of any example herein, particularly example 54 or 55, wherein the at least one lateral width comprises a plurality of lateral widths, each positioned at a different axial position along the length of the prosthetic valve.

Example 57. The computing system of any example herein, particularly example 56, wherein at least two of the plurality of lateral widths are extending between lateral junctions associated with the same cell column.

Example 58. The computing system of any example herein, particularly example 20 or 57, wherein the at least one identified cell column comprises at least two cell columns, and wherein the plurality of lateral widths comprises at least one lateral width extending between lateral junctions of each of the two cell columns.

Example 59. The computing system of any example herein, particularly one of examples 44 to 58, wherein analyzing the image to determine at least one lateral width further comprises determining at least one opening angle, and wherein the lateral width is calculated from the opening angle and a length of a strut segment.

Example 60. The computing system of any example herein, particularly example 59, wherein the opening angle is defined between two intersecting strut segments, and wherein the opening angle is facing the lateral width.

Example 61. The computing system of any example herein, particularly example 59, wherein the opening angle is defined between a strut segment and the lateral width.

Example 62. The computing system of any example herein, particularly example 43, wherein the prosthetic valve comprises a plurality of threaded rods and a plurality of nuts, each nut screwed on to a respective threaded rod, and wherein identifying structural components comprises identifying the plurality of nuts of the prosthetic valve.

Example 63. The computing system of any example herein, particularly example 62, wherein the at least one lateral width extends between a respective pair of the identified nuts of the prosthetic valve.

Example 64. The computing system of any example herein, particularly any one of examples 41 to 63, wherein the operations further comprise analyzing the image to determine at least one vertical height.

Example 65. The computing system of any example herein, particularly example 64, wherein the at least one vertical height comprises a plurality of vertical heights, and wherein the operations further comprise comparing between the vertical heights and generating data indicative of whether the expansion of the prosthetic valve is non-even.

Example 66. The computing system of any example herein, particularly any one of examples 16 to 65, wherein the constant-length structural component is an outer member of an expansion and locking assembly coupled to a frame of the prosthetic valve.

Example 67. The computing system of any example herein, particularly any one of examples 16 to 65, wherein the constant-length structural component is a strut segment of the prosthetic valve.

Example 68. The computing system of any example herein, particularly any one of examples 16 to 67, wherein estimating at least one outer diameter comprises calculating a diameter of a circumcircle surrounding an internal polygon defined between junctions disposed around the prosthetic valve at a corresponding lateral plane, wherein the length of each of the edges of the internal polygon is the lateral width determined at the axial position of the lateral plane, and wherein the calculation further includes conversion of distances from pixels to length units based at least in part on the length of the constant-length structural component.

Example 69. The computing system of any example herein, particularly example 68, wherein the calculation further includes adding a product of thickness of a junction.

Example 70. The computing system of any example herein, particularly example 69, wherein the operations further comprise a step of estimating at least one inner diameter by executing the same calculation but without adding a product of the thickness of a junction thereto.

Example 71. The computing system of any example herein, particularly any one of examples 41 to 70, wherein estimating at least one outer diameter comprises estimating at least two outer diameters, each based on a lateral width determined at a different axial position.

Example 72. The computing system of any example herein, particularly example 71, wherein estimating at least one outer diameter further comprises estimating at least one outer diameter at an axial position for which a lateral width has not been determined.

Example 73. The computing system of any example herein, particularly example 72, wherein the outer diameter at an axial position for which a lateral width has not been determined, is extrapolated from at least two outer diameters estimated from lateral widths determined at axial positions on one side thereof.

Example 74. The computing system of any example herein, particularly example 72, wherein the outer diameter at an axial position for which a lateral width has not been determined, is interpolated from at least two outer diameters estimated from lateral widths determined at axial positions on both sides thereof.

Example 75. The computing system of any example herein, particularly any one of examples 41 to 74, wherein the at least one estimated outer diameter is selected from: the inflow diameter, the outflow diameter, and/or the annular diameter.

Example 76. The computing system of any example herein, particularly any one of examples 41 to 75, wherein the operations further comprise the steps of: identifying a one or more markers: responsive to the identified one or more markers, identifying one or more commissures of the prosthetic valve; and outputting an indication of a position of the identified one or more commissures.

Example 77. The computing system of any exampled herein, particularly example 76, wherein the one or more markers comprises a plurality of eyelets, each pair of eyelets positioned on opposing sides of a respective commissure.

Example 78. The computing system of any example herein, particularly any one of examples 41 to 75, wherein the operations further comprise: identifying one or more markers; responsive to the identified one or more markers, identifying the position of the prosthetic valve; and outputting an indication of the position of the prosthetic valve.

Example 79. The computing system of any example herein, particularly example 78, wherein the one or more markers comprise one or more eyelets, each of the one or more eyelets positioned on a respective extension member extending from the prosthetic valve.

Example 80. A method of identifying a position of one or more commissures of a prosthetic valve, comprising: acquiring, by an imaging device, an image of the prosthetic valve; analyzing, by a control circuitry, the image to identify one or more markers: responsive to the identified one or more markers, identifying the one or more commissures of the prosthetic valve; and outputting an indication of a position of the identified one or more commissures.

Example 81. The method of any example herein, particularly example 80, wherein the one or more markers comprise a plurality of eyelets, each pair of eyelets positioned on opposing sides of a respective commissure.

Example 82. A computing system comprising: a control circuitry; and a memory communicatively coupled to the control circuitry and storing executable instructions that, when executed by the control circuitry, cause the control circuitry to perform operations comprising: receiving from an imaging device an image of the prosthetic valve: analyzing the image to identify one or more markers: responsive to the identified one or more markers, identifying the one or more commissures of the prosthetic valve; and outputting an indication of a position of the identified one or more commissures.

Example 83. The computing system of any example herein, particularly example 82, wherein the one or more markers comprise a plurality of eyelets, each pair of eyelets positioned on opposing sides of a respective commissure.

Example 84. A method of identifying a position of a prosthetic valve, comprising: acquiring, by an imaging device, an image of the prosthetic valve: analyzing, by a control circuitry, the image to identify one or more markers: responsive to the identified one or more markers, identifying the position of the prosthetic valve; and outputting an indication of the position of the prosthetic valve.

Example 85. The method of any example herein, particularly example 84, wherein the one or more markers comprise one or more eyelets, each of the one or more eyelets positioned on a respective extension member extending from a frame of the prosthetic valve.

Example 87. A computing system comprising: a control circuitry; and a memory communicatively coupled to the control circuitry and storing executable instructions that, when executed by the control circuitry, cause the control circuitry to perform operations comprising: receiving from an imaging device an image of the prosthetic valve: analyzing the image to identify one or more markers: responsive to the identified one or more markers, identifying the position of the prosthetic valve; and outputting an indication of a position of the prosthetic valve.

Example 88. The computing system of any example herein, particularly example 87, wherein the one or more markers comprise one or more eyelets, each of the one or more eyelets positioned on a respective extension member extending from a frame of the prosthetic valve.

It is appreciated that certain features of the invention, which are, for clarity, described in the context of separate examples, may also be provided in combination in a single example. Conversely, various features of the invention, which are, for brevity, described in the context of a single example, may also be provided separately or in any suitable sub-combination or as suitable in any other described example of the invention. No feature described in the context of an example is to be considered an essential feature of that example, unless explicitly specified as such.

Although the invention is described in conjunction with specific examples thereof, it is evident that numerous alternatives, modifications and variations that are apparent to those skilled in the art may exist. It is to be understood that the invention is not necessarily limited in its application to the details of construction and the arrangement of the components and/or methods set forth herein. Other examples may be practiced, and an example may be carried out in various ways. Accordingly, the invention embraces all such alternatives, modifications and variations that fall within the scope of the appended claims.

The invention claimed is:

1. A method of estimating at least one outer diameter of a prosthetic valve during an expansion procedure of the prosthetic valve at a target implantation site, comprising:

acquiring, by an imaging device, an image of the prosthetic valve during the expansion procedure;

analyzing, by a control circuitry, the image to determine at least one lateral width during the expansion procedure, comprising:

detecting, in the image, at least two structural components of the prosthetic valve at an axial position of the prosthetic valve; and measuring, in the image, the at least one lateral width between the detected at least two structural components;

analyzing, by the control circuitry, the image to identify a constant-length structural component;

retrieving, by the control circuitry, a length of the constant-length structural component and associating the length with the identified constant-length structural component;

estimating, by the control circuitry, at least one outer diameter of the prosthetic valve during the expansion procedure, based at least in part on the at least one lateral width determined from the image at the axial position, and the length of the constant-length structural component, wherein the estimating comprises applying a geometric relationship between the at least one outer diameter and the at least one lateral width; and outputting an indication of the estimated at least one outer diameter during the expansion procedure.

2. The method of claim 1, wherein the at least two structural components comprise two junctions of strut segments of the prosthetic valve.

3. The method of claim 2, wherein the two junctions are non-apical junctions.

4. The method of claim 2, wherein the two junctions are apical junctions.

5. The method of claim 1, wherein detecting at least two structural components comprises identification of at least one cell, and wherein the at least one lateral width extends between two laterally aligned junctions of the same cell.

6. The method of claim 5, wherein the at least one identified cell comprises at least two cell columns, and wherein the at least one lateral width comprises a plurality of lateral widths extending between lateral junctions of each of the two cell columns.

7. The method of claim 1, wherein the step of analyzing the image to determine at least one lateral width further comprises determining at least one opening angle defined between two intersecting strut segments, the opening angle facing the lateral width, and wherein the lateral width is calculated from the opening angle and a length of a strut segment.

8. The method of claim 1, wherein the step of analyzing the image to determine at least one lateral width further comprises determining at least one opening angle defined between a strut segment and the lateral width, and wherein the lateral width is calculated from the opening angle and a length of a strut segment.

9. The method of claim 1, wherein the prosthetic valve comprises a plurality of threaded rods and plurality of nuts, each nut screwed on to a respective threaded rod, wherein detecting at least two structural components comprises identifying the plurality of nuts of the prosthetic valve, and wherein the at least one lateral width extends between a respective pair of the identified nuts of the prosthetic valve.

10. The method of claim 1, wherein the at least one lateral width comprises a plurality of lateral widths, each positioned at a different axial position along a longitudinal axis of the prosthetic valve.

11. The method of claim 1, further comprising a step of analyzing, by a control circuitry, the image to determine at least one vertical height, wherein the at least one vertical height comprises a plurality of vertical heights, and wherein the method further comprises a step of comparing between the vertical heights and generating data indicative of whether an expansion of the prosthetic valve is non-even.

12. The method of claim 1, wherein the constant-length structural component is an outer member of an expansion and locking assembly coupled to a frame of the prosthetic valve.

13. The method of claim 1, wherein the constant-length structural component is a strut segment of the prosthetic valve.

14. The method of claim 1, wherein the step of estimating at least one outer diameter comprises calculating a diameter of a circumcircle surrounding an internal polygon defined between junctions disposed around the prosthetic valve at a corresponding lateral plane, wherein the length of each edge of the internal polygon is the lateral width determined at the axial position of the lateral plane, and wherein the calculation further includes conversion of distances from pixels to length units based at least in part on the length of the constant-length structural component.

15. The method of claim 1, wherein the step of estimating at least one outer diameter comprises estimating at least two outer diameters, each based on a lateral width determined at a different axial position.

16. A computing system for estimating at least one outer diameter of a prosthetic valve during an expansion procedure of the prosthetic valve at a target implantation site, comprising:

a control circuitry; and a memory communicatively coupled to the control circuitry and storing executable instructions that, when executed by the control circuitry, cause the control circuitry to perform operations comprising:

receiving an image, acquired by an imaging device, of the prosthetic valve during the expansion procedure;

analyzing the image to determine at least one lateral width during the expansion procedure, comprising:

detecting, in the image, at least two structural components of the prosthetic valve at an axial position of the prosthetic valve; and measuring, in the image, the at least one lateral width between the detected at least two structural components;

analyzing the image to identify a constant-length structural component;

retrieving a length of the constant-length structural component and associating the length with the identified constant-length structural component;

estimating at least one outer diameter of the prosthetic valve, based at least in part on the at least one lateral width determined from the image at the axial position, and the length of the constant-length structural component, wherein the estimating comprises applying a geometric relationship between the at least one outer diameter and the at least one lateral width; and outputting an indication of the estimated at least one outer diameter during the expansion procedure.

17. The computing system of claim 16, wherein the at least two structural components comprise two junctions of strut segments of the prosthetic valve.

18. The computing system of claim 17, wherein the two junctions are non-apical junctions.

19. The computing system of claim 16, wherein detecting at least two structural components comprises identification of at least one cell, and wherein the at least one lateral width extends between two laterally aligned junctions of the same cell.

20. The computing system of claim 16, wherein the at least one lateral width comprises a plurality of lateral widths, each positioned at a different axial position along a longitudinal axis of the prosthetic valve.

21. The computing system of claim 16, wherein measuring the at least one lateral width between the detected at least two structural components includes measuring one or more distances in pixels; and estimating at least one outer diameter of the prosthetic valve includes conversion of the one or more distances from pixels to length units based at least in part on the length of the constant-length structural component.

22. The method of claim 1, wherein measuring the at least one lateral width between the detected at least two structural components includes measuring one or more distances in pixels; and estimating at least one outer diameter of the prosthetic valve includes conversion of the one or more distances from pixels to length units based at least in part on the length of the constant-length structural component.

* * * * *